US011369695B2

(12) United States Patent
John et al.

(10) Patent No.: US 11,369,695 B2
(45) Date of Patent: Jun. 28, 2022

(54) FAT DROPLETS IN RETINA AND OPTIC NERVE AS A DIAGNOSTIC MARKER FOR NEURODEGENERATION AND GLAUCOMA IN HUMANS

(71) Applicant: The Jackson Laboratory, Bar Harbor, ME (US)

(72) Inventors: Simon W. M. John, Bar Harbor, ME (US); Peter Alexander Williams, Tremont, ME (US)

(73) Assignee: The Jackson Laboratory, Bar Harbor, ME (US)

( * ) Notice: Subject to any disclaimer, the term of this patent is extended or adjusted under 35 U.S.C. 154(b) by 0 days.

(21) Appl. No.: 16/466,348

(22) PCT Filed: Dec. 4, 2017

(86) PCT No.: PCT/US2017/064504
§ 371 (c)(1),
(2) Date: Jun. 4, 2019

(87) PCT Pub. No.: WO2018/106594
PCT Pub. Date: Jun. 14, 2018

(65) Prior Publication Data
US 2020/0197539 A1 Jun. 25, 2020

Related U.S. Application Data

(60) Provisional application No. 62/429,950, filed on Dec. 5, 2016.

(51) Int. Cl.
*A61K 49/00* (2006.01)
*A61B 3/10* (2006.01)
*A61B 3/12* (2006.01)
*A61B 3/13* (2006.01)
*A61K 9/00* (2006.01)

(52) U.S. Cl.
CPC .......... *A61K 49/0017* (2013.01); *A61B 3/102* (2013.01); *A61B 3/12* (2013.01); *A61B 3/13* (2013.01); *A61K 9/0014* (2013.01); *A61K 9/0019* (2013.01); *A61K 2123/00* (2013.01)

(58) Field of Classification Search
CPC .............. A61K 49/0017; A61K 9/0014; A61K 9/0019; A61K 2123/00; A61B 3/102; A61B 3/12; A61B 3/13
See application file for complete search history.

(56) References Cited

U.S. PATENT DOCUMENTS

| 5,789,169 A | 4/1998 | Nyguyen et al. |
| 5,976,502 A | 11/1999 | Khoobehi et al. |
| 2010/0003707 A1 | 1/2010 | Ghaffariyeh |
| 2010/0034749 A1 | 2/2010 | Schulze et al. |
| 2011/0294891 A1 | 12/2011 | Widder et al. |
| 2013/0172204 A1 | 7/2013 | Grus et al. |
| 2016/0339043 A1* | 11/2016 | Lee .................... A61K 47/20 |

FOREIGN PATENT DOCUMENTS

WO 2013163758 A1 11/2013

OTHER PUBLICATIONS

Dissertation of Judy V. Nguyen,"Phagocytic Astrocytes and the Formation of Lipid Droplets in the Myelination Transistion Zone of the Optic Nerve Head in the DBA/2J Mouse Glaucoma Model," Aug. 2014. (Year: 2014).*
International Preliminary Report on Patentability and Written Opinion of The International Searching Authority dated Jun. 11, 2019 from corresponding PCT Application No. PCT/US2017/064504.
Bonilla et al, "Application of Nile Blue and Nile Red, Two Fluorescent Probes, for Detetction of Lipid Droplets in Human Skeletal Muscle." The Journal of Histochemistry and Cytochemistry, 35(5): 619-621, 1987.
Freudiger et al., "Label-Free Biomedical Imaging with High Sensitivity by Stimulated Raman Scattering Microscopy." Science. Dec. 19, 2008; 322(5909): 1857-1861. doi: 10.1126/science. 1165758.
Greenspan, et al., "Nile Red: A Selective Fluorescent Stain for Intracellular Lipid Droplets." The Journal of Cell Biology, vol. 100, Mar. 1985; pp. 965-973.
Ishizawa, et al., "Real-time identification of liver cancers by using indocyanine green fluorescent imaging." Cancer vol. 115, Issue 11 2491-2504, 2009.
Kosaka et al.,"Near infrared fluorescence-guided real-time endoscopic detection of peritoneal ovarian cancer nodules using intravenously injected indocyanine green." Int. J. Cancer: 129, 1671-1677 (2011) 2011.
Lee, et al., "Synthesis of a new fluorescent small molecule probe and its use for in vivo lipid imaging." Chem. Commun., 2011, 47, 7500-7502. plus Supporting Information document p. 1-13.
Merian et al., "Fluorescent Nanoprobes Dedicated to in Vivo Imaging: From Preclinical Validations to Clinical Translation." Molecules 2012, 17, 5564-5591, doi:10.3390/molecules17055564.
Rice et al., "Fluorescence Imaging of Interscapular Brown Adipose Tissue in Living Mice." Journal of Materials Chemistry B, 34 pages. , 2015.
Schadlich et al., "How Stealthy are PEG-PLA Nanoparticles? An NIR In Vivo Study Combined with Detailed Size Measurements." Pharm Res (2011) 28:1995-2007.
Spandl, et al. "Live Cell Multicolor Imaging of Lipid Droplets with a New Dye, LD540." Traffic vol. 10, Issue 11 1579-84, 2009.
Strong, N.P., "How optometrists screen for glaucoma: A survey." Ophthalmic & Physiological Optics, vol. 12, Issue 1, Jan. 1992 pp. 3-7.
Tuck, M.W. et al., "Relative effectiveness of different modes of glaucoma screening in optometric practice." Ophthalmic & Physiological Optics, vol. 13, Issue 3, Jul. 1993, pp. 227-232.
Vinegoni, et al., "Indocyanine Green Enables Near-Infrared Fluorescence Imaging of Lipid-Rich, Inflamed Atherosclerotic Plaques." Sci Transl Med. May 25, 2011; 3(84): 84ra45. doi:10.1126/scitranslmed.300157.

(Continued)

*Primary Examiner* — Robert S Cabral
(74) *Attorney, Agent, or Firm* — Pierce Atwood LLP

(57) ABSTRACT

The present invention relates to the use of lipid/fat droplet deposits in retinas of a human subject as a biomarker for diagnosing, prognosing, and/or monitoring retinal neurodegeneration with or without an elevated intraocular pressure in glaucoma.

19 Claims, 9 Drawing Sheets

(56) References Cited

OTHER PUBLICATIONS

Wang et al., "In vivo intravascular ultrasound-guided photoacoustic imaging of lipid in plaques using an animal model of atherosclerosis." Ultrasound Med Biol. Dec. 2012; 38(12): 2098-2103.

Yang, et al., "Monodansylpentane as a Blue-Fluorescent Lipid-Droplet Marker for Multi-Color Live-Cell Imaging." PLoS One. 2012; 7(3): e32693. Published online Mar. 1, 2012. doi: 10.1371/journal.pone.0032693.

Office Action dated Oct. 13, 2021 from corresponding European Patent Application No. 17835890.9.

Nguyen "Phagocytic Astrocytes and the Formation of Lipid Droplets in the Myelination Transition Zone of the Optic Nerve Head in the DBA/2J Mouse Glaucoma Model", John Hopkins University Dissertation Abstract, Aug. 2014, 3 pages.

Li, et al., Biological Chemistry, Harbin Institute of Technology Press, Sep. 2005, p. 57-58 (Reference in Chinese, English translation attached).

Osborne "Pathogenesis of ganglion "cell death" in glaucoma and neuroprotection: focus on ganglion cell axonal mitochondria" Chapter 24, Progress in Brain Research, vol. 173, 2008, 14 pages.

\* cited by examiner

FAT DROPLETS IN RETINA AND OPTIC NERVE AS A DIAGNOSTIC MARKER FOR NEURODEGENERATION AND GLAUCOMA IN HUMANS

REFERENCE TO RELATED APPLICATIONS

This application claims priority under 35 U.S.C. § 371 to International application number PCT/US2017/064504 filed Dec. 4, 2017, which claims benefit under 35 U.S.C. § 119(e) of U.S. Provisional Application No. 62/429,950, filed on Dec. 5, 2016, the entire content of each of which is incorporated by reference herein.

STATEMENT REGARDING FEDERALLY SPONSORED RESEARCH

The present invention was made with U.S. government support under Grant No. R01 EY011721, awarded by the National Institute of Health (NIH). The U.S. government has certain rights in the invention.

BACKGROUND OF THE INVENTION

Glaucoma is an ocular disorder affecting more than 70 million people world-wide and is characterized by cupping of the optic disc due to loss of retinal ganglion cells (RGCs) and the corresponding axons leading to progressive visual loss. It is the leading cause of preventable blindness in the United States. Primary Open Angle Glaucoma ("POAG") is the most common form of glaucoma.

Several methods are currently available to screen if a human suffers from glaucoma. Glaucoma pathology is often associated with changes to the trabecular meshwork, a structure associated with aqueous humor outflow from the eye. Decreases in aqueous humor outflow can cause increases in intraocular pressure (IOP). Continuously elevated IOP has been associated with the progressive deterioration of the retina and the loss of visual function. Increased IOP is a readily measurable characteristic of glaucoma, the diagnosis of the disease is largely screened for by measuring IOP (Strong, *Ophthal Physiol Opt.* 12:3-7, 1992). Tonometry is most commonly used to measure elevated IOP and to assess the risk of glaucoma.

However, elevated IOP is not a reliable predictor for glaucoma. Only 76% of glaucomatous patients have high IOP (>21 mmHg), and 16% of glaucomatous patients present with apparent loss of visual function yet have normal IOP. On the other hand, and very importantly, not everyone who has high IOP develops glaucoma. While some patients are susceptible to high IOP, and go on to develop glaucoma, other patients are apparently resistant to high IOP, and do not develop glaucoma. Currently, there is not way to distinguish these two groups of patients before there is evident visual system disease. Furthermore, glaucomatous and normal pressure ranges often overlap, thus such methods have limited diagnostic value unless multiple readings are obtained (Tuck et al, *Ophthal. Physiol Opt.* 13:227-232, 1993).

Patients with ocular hypertension are considered at a high risk for eventually developing the visual loss associated with glaucoma. As a general rule, conventional therapy of lowering IOP is an objective for the treatment of glaucoma patients and for patients with ocular hypertension in order to decrease the potential for, or severity of, glaucomatous retinopathy. However, it has been observed that disease progression may continue despite significant IOP reduction.

Clearly, modulation of the primary risk factor of glaucoma, such as elevated IOP alone, is not enough to completely prevent the RGC loss. The therapy fails to address the neurodegenerative processes involved in glaucoma directly. Hence, only a targeted therapeutic intervention that can prolong the survival of RGCs and possibly regenerate the lost RGCs, will successfully preserve the vision in glaucoma patients.

Ophthalmoscopy is a highly subjective procedure to examine optic nerve head morphology, but the procedure demands sophisticated clinical skills by a physician. Over half of the patient population with glaucoma are unaware of the disease state, and have already lost approximately 30-50% of retinal ganglion cells by the time of diagnosis. Perimetry permits diagnosis of visual field loss, an indicator of ganglion cell death in retina. However, this method precludes its use as an early detector for glaucoma, largely because it can only detect severe nerve damages occurred at an advanced glaucomatous stage.

Few other alternative diagnostic approaches have been proposed. To that end, U.S. Pat. No. 5,789,169 discloses novel cDNAs and protein sequences highly induced by glucocorticoids in endothelial cells, purportedly serving as diagnostic biomarkers for glaucoma. U.S. 2013/0172204 A1 discloses the use of autoantibodies for glaucoma diagnosis. U.S. 2010/0003707 A1 discloses Brian Derived Neurotropic Factor (BDNF) as an early biomarker for glaucoma.

There is a continuing need to identify reliable biomarkers useful in screening patients at risk for glaucoma and accurately detect neurodegeneration at the early stage of glaucoma before vision loss occurs. Glaucoma that is detected early and treated promptly would have reduced or reversible loss of visual function. Accordingly, the industry is in an urgent need for an improved diagnostic method for the early diagnosis of neurodegeneration in RGC and retina as well as glaucoma.

SUMMARY OF THE INVENTION

It is an object of the present invention to provide a method for diagnosing glaucoma in a patient which comprises the steps: (a) providing a patient in needs of diagnosing glaucoma; (b) detecting the presence of fat droplets in the retina and/or optic nerve of the patient, wherein the presence of the fat droplets is predictive of the occurrence of glaucoma (diagnostic of glaucoma). The method of the invention allows better focus on caring for those who will develop glaucoma, while avoiding unnecessary medication of those who will not.

It is another object of the present invention to provide a method for diagnosing retinal and/or optic nerve neurodegeneration in a patient which comprises the steps: (a) providing a patient in needs of diagnosing neurodegeneration in retina; (b) detecting the presence of fat droplets in the retina region and/or optic nerve region of the patient, wherein the presence of the fat droplets is predictive of the neurodegeneration in retina and/or optic nerve.

It is another object of the present invention to provide a method for prognosing glaucoma in a patient which comprises the steps: (a) providing a patient suffering from a high intraocular pressure (IOP); (b) detecting the presence of fat droplets in the retina and/or optic nerve of the patient, wherein the presence of the fat droplets is prognostic of glaucoma.

It is another object of the present invention to provide a method for prognosing ocular neurodegeneration in the retina and/or optic nerve of a patient, which comprises the steps: (a) providing a patient suffering from a high intraocular pressure (IOP); (b) detecting the presence of fat droplets in the retina and/or optic nerve of the patient, wherein the presence of the fat droplets is prognostic of neurodegeneration in retina and/or optic nerve.

It is another object of the present invention to provide a method for monitoring glaucoma in a patient (e.g., a human patient).

It is another object of the present invention to provide a method of monitoring neurodegeneration in the retina in a patient (e.g., a human patient).

It is another object of the present invention to provide a method of monitoring neurodegeneration in the optic nerve in a patient (e.g., a human patient).

It is another object of the present invention to provide fat droplet marker capable of specifically detecting glaucoma.

It is another object of the present invention to provide fat droplet marker capable of specifically detecting neurodegeneration in retina and/or optic nerve, or future neurodegeneration or neural dysfunction in the same.

It is another object of the present invention to provide a method of treating glaucoma, which comprises administering to a glaucomatous patient an effective amount of an agent that inhibits the synthesis of a fat droplet in the retina and/or optic nerve, thereby treating glaucoma.

It is another object of the present invention to provide a method of treating neurodegeneration in retina, which comprises administering to a glaucomatous patient an effective amount of an agent that inhibits the synthesis of a fat droplet in the retina and/or optic nerve, thereby treating neurodegeneration in retina.

Representative aspects and embodiments of the present invention are also described in the numbered paragraphs below.

1. A method for diagnosing ocular neurodegeneration in a subject, the method comprising the steps of:
   a) providing a subject suspected of having ocular neurodegeneration; and,
   b) detecting the presence of fat droplets in a retinal region and/or optic nerve region of said subject,
   wherein the presence of fat droplets in the retinal region and/or optic nerve region of said subject is indicative of ocular neurodegeneration.
2. The method of paragraph 1, wherein said ocular neurodegeneration is retinal neurodegeneration.
3. The method of paragraph 1, wherein said ocular neurodegeneration is optic nerve neurodegeneration.
4. The method of paragraph 1, wherein step b) comprises:
   i) administering a fluorescent dye to the subject; and,
   ii) detecting the presence of fat droplets in the retinal region and/or optic nerve region of said subject based on the fluorescence of the fluorescent dye,
   wherein the presence of fat droplets in the retinal region and/or optic nerve region of said subject, as indicated by fluorescence of the fluorescent dye, is indicative of retinal and/or optic nerve neurodegeneration.
5. The method of paragraph 4, wherein the fluorescent dye is a lipophilic dye, such as Oil Red O, Nile Blue, Nile Red, SRFluor680, LD540, LipidGreen, ICG/indocyanine green, or fluorescent nanoprobe.
6. The method of paragraph 4, wherein the fluorescent dye is Nile Red or Indocyanine green (ICG).
7. The method of paragraph 4, wherein the subject is having glaucoma, high IOP, or at risk of having glaucoma.
8. The method of paragraph 7, wherein the subject is having glaucoma (e.g., early stage glaucoma).
9. The method of paragraph 4, wherein the fluorescent dye is administered to the eye of the subject by intravitreal injection, intravenous injection, topical application, or iontophoresis.
10. The method of paragraph 4, wherein the fluorescent dye is administered into the eye two or more times (e.g., 2, 3, 4, 5, 6, 7, 8, 9, 10 times or more).
11. The method of paragraph 4, wherein the fluorescent dye is detected after a set period time post administration of the fluorescent dye, wherein the set period of time is 3-5 minutes, about 10 minutes, 20-60 minutes, 1-3 hrs, 5-10 hrs, 12-24 hrs, 1 day, 2 days, 3 days, 4 days, 5 days or more.
12. The method of paragraph 4, wherein the fluorescent dye is detected in vivo using a non-invasive detection method selected from the group consisting of: Scanning Laser Ophthalmoscopy (SLO), fundoscopy (such as a fluorescent fundal imaging modality), and biomicroscope.
13. The method of paragraph 12, wherein the non-invasive detection method is Scanning Laser Ophthalmoscopy (SLO).
14. The method of paragraph 1, wherein said subject has a normal IOP value of <21 mmHg.
15. The method of paragraph 1, wherein said subject has an elevated IOP value of ≥21 mmHg.
16. The method of paragraph 1, wherein said subject is an adult human.
17. The method of paragraph 16, wherein said adult human is over age 40, 50, or 60.
18. The method of paragraph 1, wherein said subject has no signs or symptoms of glaucoma, but is associated with a risk factor for developing glaucoma selected from the group consisting of: intraocular pressure (IOP), age, race or ethnic background, family history, gender, medical condition (diabetes, heart disease, high blood pressure and sickle cell anemia), eye condition (myopia, hyperopia), eye injury or surgery, early estrogen deficiency, corneal thickness, and corticosteroid medication (eye droplets over long period of time).
19. The method of paragraph 1, wherein said subject is a patient seeking routine annual eye examination.
20. The method of paragraph 1, wherein step b) is carried out using fundoscopy, OCT (Optical coherence tomography), Scanning Laser Ophthalmoscopy (SLO), Adaptive Optics SLO (AOSLO), or Ramen spectroscopy, optionally in combination with using one or more fluorescent marker dyes or other agents that highlight the lipid droplets.
21. The method of paragraph 1, further comprising selecting the subject for receiving treatment for glaucoma when said retinal region is found to have fat droplets.
22. A method for diagnosing glaucoma, the method comprising the steps of:
   a) providing a subject in needs of diagnosing glaucoma; and,
   b) detecting the presence of fat droplets in a retinal region and/or optic nerve region of said subject,
   wherein the presence of fat droplets in the retinal region and/or optic nerve region of said subject is predictive of neurodegeneration and occurrence of glaucoma.
23. The method of paragraph 22, wherein step b) comprises:
   i) administering a fluorescent dye to the subject; and,
   ii) detecting the presence of fat droplets in the retinal region and/or optic nerve region of said subject based on the fluorescence of the fluorescent dye,
   wherein the presence of fat droplets in the retinal region and/or optic nerve region of said subject is indicated by fluorescence of the fluorescent dye.

24. The method of paragraph 22, wherein said glaucoma is primary open angle glaucoma.
25. The method of paragraph 22, wherein said subject has a normal IOP value of <21 mmHg.
26. The method of paragraph 22, wherein said subject has an elevated IOP value of ≥21 mmHg.
27. The method of paragraph 22, wherein said subject is an adult human.
28. The method of paragraph 27, wherein said adult human is over age 40, 50, or 60.
29. The method of paragraph 22, wherein said subject has no signs or symptoms of glaucoma, but is associated with a risk factor for developing glaucoma selected from the group consisting of: intraocular pressure (IOP), age, race or ethnic background, family history, gender, medical condition (diabetes, heart disease, high blood pressure and sickle cell anemia), eye condition (myopia, hyperopia), eye injury or surgery, early estrogen deficiency, corneal thickness, and corticosteroid medication (eye droplets over long period of time).
30. The method of paragraph 22, wherein said subject is a patient seeking routine annual eye examination.
31. The method of paragraph 22, wherein step b) is carried out using fundoscopy, OCT (Optical coherence tomography), Scanning Laser Ophthalmoscopy (SLO), Adaptive Optics SLO (AOSLO), or Ramen spectroscopy, optionally in combination with using one or more fluorescent marker dyes or other agents that highlight the lipid droplets.
32. A method for prognosing ocular neurodegeneration in glaucoma, the method comprising the steps of:
   a) providing a subject having glaucoma and/or having a high intraocular pressure (IOP); and,
   b) detecting the presence and optionally the amount of fat droplets in a retinal region and/or optic nerve region of said subject,
      wherein the presence and optionally the amount of fat droplets in the retinal region and/or optic nerve region of said subject is prognostic of ocular neurodegeneration in glaucoma.
33. The method of paragraph 32, wherein step b) comprises:
   i) administering a fluorescent dye to the subject; and,
   ii) detecting the presence and optionally the amount of fat droplets in the retinal region and/or optic nerve region of said subject based on the fluorescence of the fluorescent dye,
      wherein the presence and optionally the amount of fat droplets in the retinal region and/or optic nerve region of said subject is indicated by fluorescence of the fluorescent dye.
34. The method of paragraph 32, wherein said glaucoma is primary open angle glaucoma.
35. The method of paragraph 32, wherein said subject has a normal IOP value of <21 mmHg.
36. The method of paragraph 32, wherein said subject has an elevated IOP value of ≥21 mmHg.
37. The method of paragraph 32, wherein said subject is an adult human.
38. The method of paragraph 37, wherein said adult human is over age 40, 50, or 60.
39. The method of paragraph 32, wherein said subject is a patient seeking routine annual eye examination.
40. The method of paragraph 32, wherein step b) is carried out using fundoscopy, OCT (Optical coherence tomography), Scanning Laser Ophthalmoscopy (SLO), Adaptive Optics SLO (AOSLO), or Ramen spectroscopy, optionally in combination with using one or more fluorescent marker dyes or other agents that highlight the lipid droplets.
41. A method for prognosing glaucoma, the method comprising the steps of:
   a) providing a subject having glaucoma and/or having a high intraocular pressure (IOP); and,
   b) detecting the presence and optionally the amount of fat droplets in a retinal region and/or optic nerve region of said subject,
      wherein the presence and optionally the amount of fat droplets in the retinal region and/or optic nerve region of said subject is prognostic of glaucoma.
42. The method of paragraph 41, wherein step b) comprises:
   i) administering a fluorescent dye to the subject; and,
   ii) detecting the presence and optionally the amount of fat droplets in the retinal region and/or optic nerve region of said subject based on the fluorescence of the fluorescent dye,
      wherein the presence and optionally the amount of fat droplets in the retinal region and/or optic nerve region of said subject is indicated by fluorescence of the fluorescent dye.
43. A method for monitoring ocular neurodegeneration in glaucoma, the method comprising the steps of:
   a) providing a subject having neurodegeneration in glaucoma; and,
   b) detecting the presence and optionally the amount of fat droplets in a retinal region and/or optic nerve region of said subject,
      wherein the presence and optionally the amount of fat droplets in the retinal region and/or optic nerve region of said subject is indicative of the status or progression of neurodegeneration in glaucoma.
44. The method of paragraph 43, wherein step b) comprises:
   i) administering a fluorescent dye to the subject; and,
   ii) detecting the presence and optionally the amount of fat droplets in the retinal region and/or optic nerve region of said subject based on the fluorescence of the fluorescent dye,
      wherein the presence and optionally the amount of fat droplets in the retinal region and/or optic nerve region of said subject is indicated by fluorescence of the fluorescent dye.
45. The method of paragraph 43, wherein said subject has been treated for glaucoma.
46. The method of paragraph 43, wherein said subject is being treated for glaucoma.
47. A method for monitoring glaucoma, the method comprising the steps of:
   a) providing a subject having glaucoma; and,
   b) detecting the presence and optionally the amount of fat droplets in a retinal region and/or optic nerve region of said subject,
      wherein the presence and optionally the amount of fat droplets in the retinal region and/or optic nerve region of said subject is indicative of the status or progression of glaucoma.
48. The method of paragraph 47, wherein step b) comprises:
   i) administering a fluorescent dye to the subject; and,
   ii) detecting the presence and optionally the amount of fat droplets in the retinal region and/or optic nerve region of said subject based on the fluorescence of the fluorescent dye,
      wherein the presence and optionally the amount of fat droplets in the retinal region and/or optic nerve region of said subject is indicated by fluorescence of the fluorescent dye.
49. The method of paragraph 47, wherein said subject has been treated for glaucoma.
50. The method of paragraph 47, wherein said subject is being treated for glaucoma.

51. A method of treating glaucoma in a subject in need thereof, comprising the steps of:
  (1) using the method of any one of paragraphs 10-18, selecting a subject for receiving treatment for glaucoma; and,
  (2) administering to the subject a therapeutically effective amount of a composition comprising an agent selected from the group consisting of nicotinamide (NAM), NMN, NAD, pyruvate, and PQQ, thereby treating glaucoma.

52. The method of paragraph 51, further comprising the step of administering a gene composition, wherein said gene composition comprising a polynucleotide encoding nmnat1.

53. The method of paragraph 51, further comprising administering to the subject an additional therapeutic agent selected from the group consisting of: a beta blocker, a nonselective adrenergic agonist, a selective α-2 adrenergic agonist, a Carbonic Anhydrase Inhibitor (CAI), a prostaglandin analog, a parasympathomimetic agonist, a carbachol or a combination thereof.

54. A method for identifying a compound for the treatment of ocular neurodegeneration and/or elevated intraocular pressure in glaucoma, the method comprising the steps of:
  a) providing a candidate compound;
  b) administering the candidate compound to a subject having ocular neurodegeneration and/or elevated intraocular pressure;
  c) detecting the presence and optionally the amount of fat droplets in a retinal region and/or optic nerve region of said subject;
  wherein the absence, or a decrease of the amount, of fat droplets in the retinal region and/or optic nerve region of said subject after administering the candidate compound, as compared to a control subject not administered the candidate compound, identifies the candidate compound as being the compound for the treatment of ocular neurodegeneration and/or elevated intraocular pressure in glaucoma.

55. The method of paragraph 54, wherein said subject is a DBA/2J mouse.

56. The method of paragraph 54, wherein the presence or absence, or the amount of the fat droplets, is determined by fundoscopy, OCT (Optical coherence tomography), Scanning Laser Ophthalmoscopy (SLO), Adaptive Optics SLO (AOSLO), or Ramen spectroscopy, optionally in combination with using one or more fluorescent marker dyes or other agents that highlight the lipid droplets.

57. The method of paragraph 54, wherein the presence or absence, or the amount of the fat droplets, is determined via a biopsy obtained from said retina region.

58. A method for screening for a compound for use as a therapeutic agent to treat ocular neurodegeneration in glaucoma or to treat elevated intraocular pressure, the method comprising the steps of:
  a) providing a candidate compound;
  b) administering the candidate compound to a subject having ocular neurodegeneration in glaucoma and/or elevated intraocular pressure;
  c) detecting the presence and optionally the amount of fat droplets in a retinal region and/or optic nerve region of said subject;
  wherein the absence, or a decrease of the amount, of fat droplets in the retinal region and/or optic nerve region of said subject after administering the candidate compound, as compared to a control subject not administered the candidate compound, identifies the candidate compound as being the compound for use as the therapeutic agent to treat ocular neurodegeneration in glaucoma or to treat elevated intraocular pressure.

59. The method of paragraph 58, wherein step c) comprises:
  i) administering a fluorescent dye to the subject; and,
  ii) detecting the presence and optionally the amount of fat droplets in the retinal region and/or optic nerve region of said subject based on the fluorescence of the fluorescent dye,
  wherein the presence and optionally the amount of fat droplets in the retinal region and/or optic nerve region of said subject is indicated by fluorescence of the fluorescent dye.

The foregoing brief summary broadly describes the features and technical advantages of certain embodiments of the present invention. It should be understood that all embodiments described herein could be combined with any other embodiment unless explicitly disclaimed. Additional features and technical advantages will be described in the detailed description of the invention with any accompanying figures that follows.

Figure 5A:
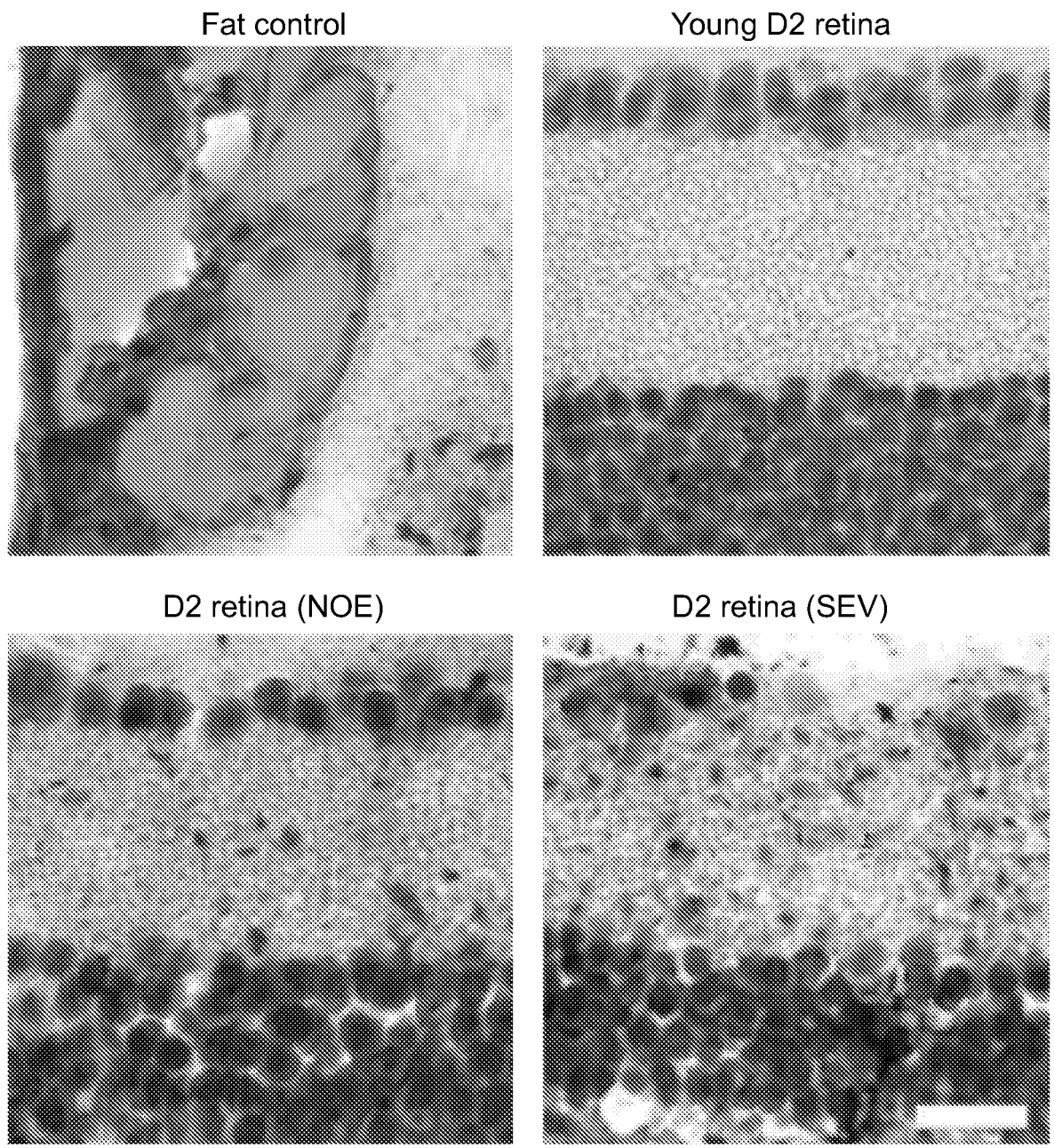

FIG. 5A shows inner-retina extracellular lipid/fat droplet formation in IOP-insulted, aged D2 eyes as stained using Oil Red O. Staining was present in D2 eyes which had both no (NOE) or severe (SEV) optic nerve degeneration. Extraocular fat was used as a positive control (n=6/group). Scale bar=25 μm.

Figure 5B:
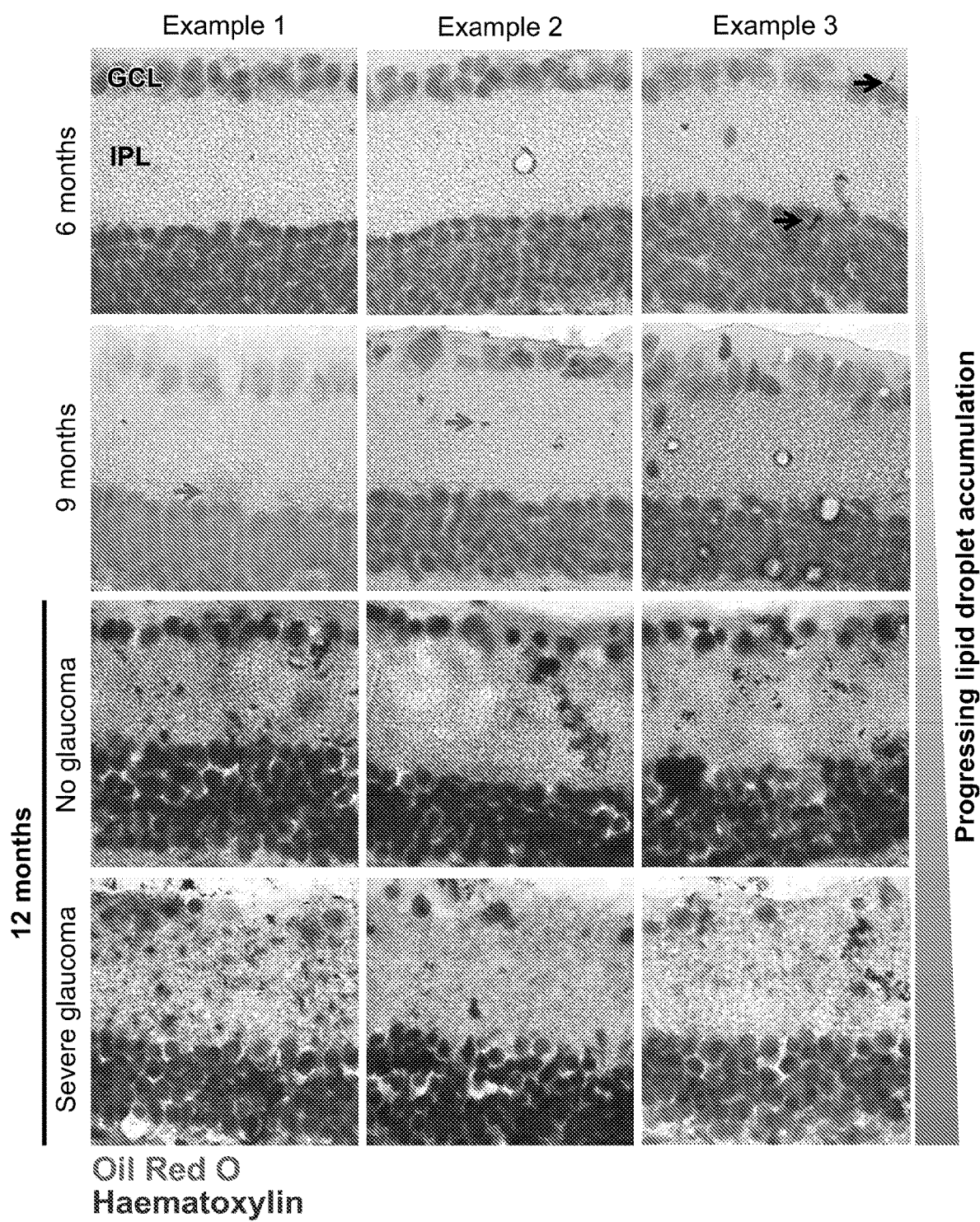

FIG. 5B shows progression of lipid droplet formation in DBA/2J retinas. Lipid droplet formation in the inner retina was assessed by Oil Red O staining, which brightly stained neutral triglycerides and lipids. Following intraocular pressure elevation, lipid droplets were present within the inner retina of DBA/2J mice. At 6 months of age, the majority of retinas were negative for lipid droplets. By 9 months of age, small and dispersed lipid droplets were present in some eyes. By 12 months of age, lipid accumulation was present in the majority of eyes in retinas that had not yet developed glaucoma (no glaucoma). In eyes that had developed severe glaucoma, lipid droplets were present across the retina in the majority of eyes. GCL=ganglion cell layer (retinal ganglion cell bodies), IPL=inner plexiform layer (retinal ganglion cell dendrites and synapses). Haematoxylin (dark blue/purple) is a general marker of cell nuclei used as a counter-stain.

Figure 6:
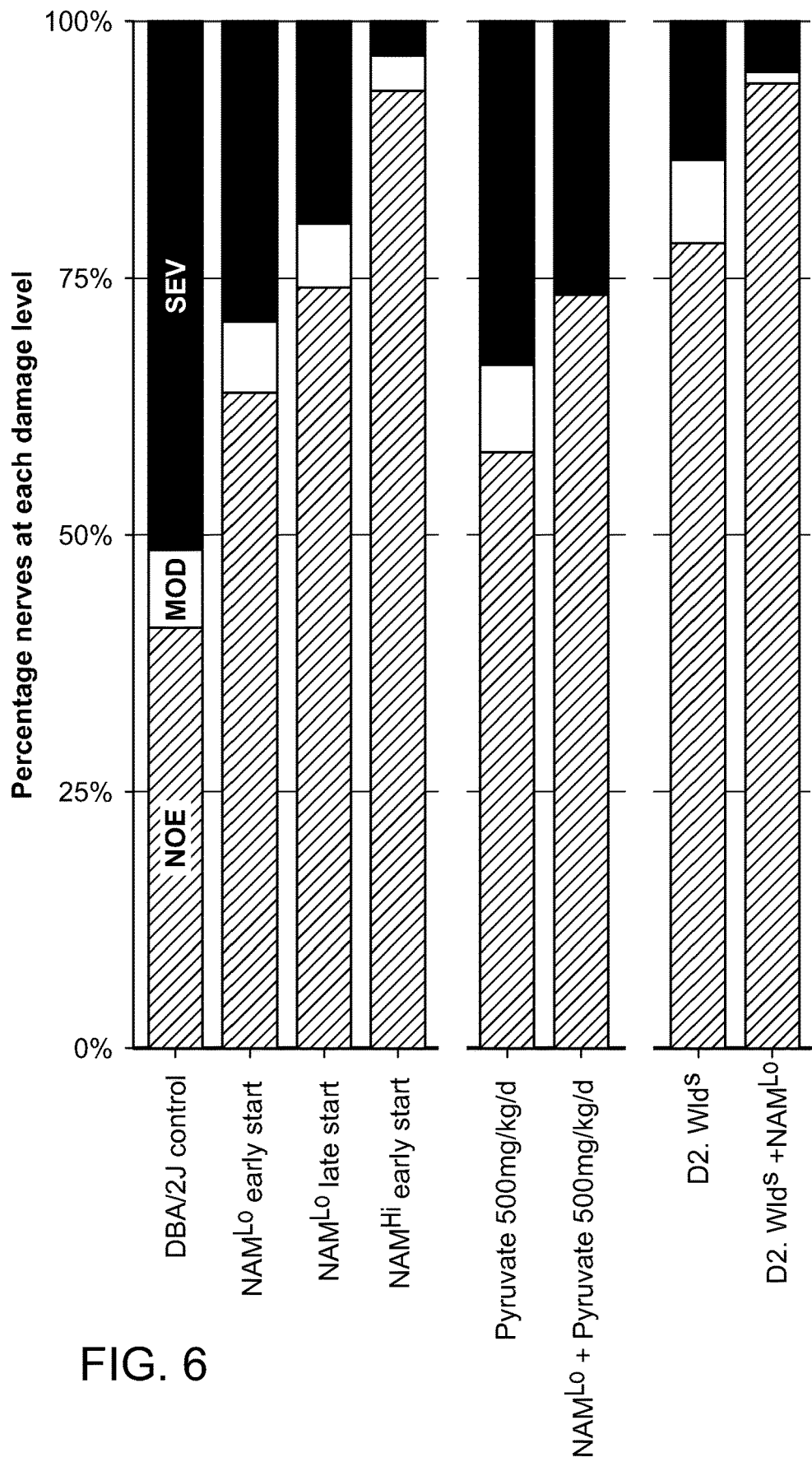

FIG. 6 shows that nicotinamide protects against optic nerve degeneration in D2 glaucoma at 12 months of age. Chart shows percentage of nerves with no detectable glaucoma (NOE; lower sections of the bars), moderate glaucomatous damage (MOD; middle sections of the bars), or severe glaucomatous damage (SEV; top sections of the bars). From left, DBA/2J control—D2 mice on standard drinking water; Nicotinamide(NAM$^{Lo}$) early start—D2 mice on standard drinking water supplemented with 550 mg/kg/day NAM from 6 months of age (pre-disease); Nicotinamide)(NAM$^{Lo}$) late start—D2 mice on standard drinking water supplemented with 550 mg/kg/day NAM from 9 months of age (during disease); Nicotinamide (NAM$^{Hi}$) early start—D2 mice on standard drinking water supplemented with 2,000 mg/kg/day NAM from 6 months of age (pre-disease); Pyruvate—D2 mice on standard drinking water supplemented with 500 mg/kg/day pyruvate from 6 months of age (pre-elevated IOP); NAM$^{Lo}$+Pyruvate—D2 mice on standard drinking water supplemented with 550 mg/kg/day NAM+500 mg/kg/day pyruvate from 6 months of age (pre-disease); D2.Wld$^S$—D2 mice carrying the Wld$^S$ transgene (altered NMNAT enzyme that enhances enzymatic activity) on standard drinking water; D2.Wld$^S$+Nicotinamide)(NAM$^{Lo}$)—D2 mice carrying the Wld$^S$ transgene (altered NMNAT enzyme) on standard drinking water with 550 mg/kg/day NAM from 6 months of age (pre-elevated IOP). Note that in addition to treating glaucomatous neurodegeneration interventionally, NAM also protects against glaucomatous neurodegeneration prophylactically.

Figure 7:
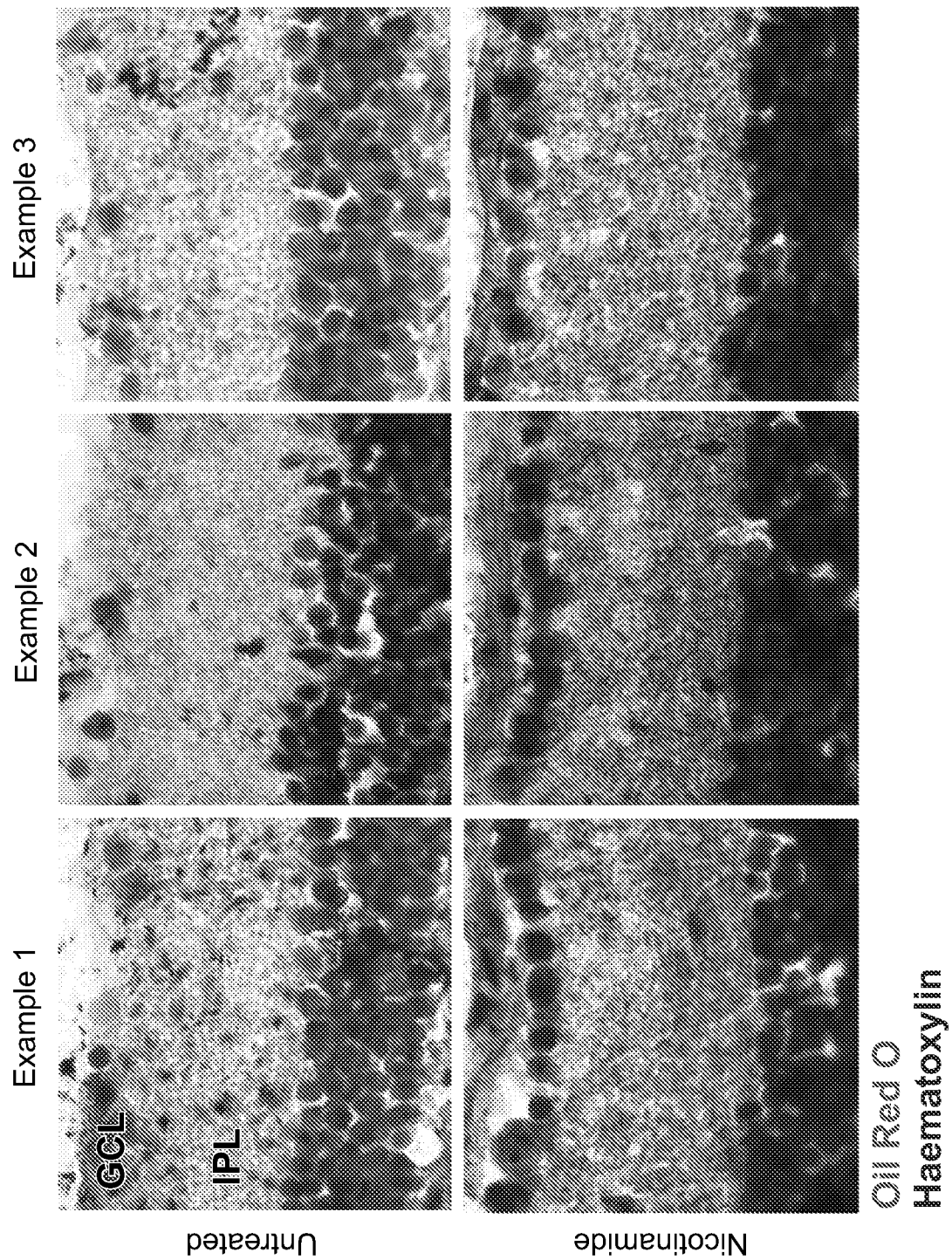

FIG. 7 shows that nicotinamide (NAM) prevents lipid deposit accumulation in DBA/2J retinas. Lipid droplet formation was assessed in retinas from nicotinamide-treated DBA/2J mice. Lipid droplet accumulation (red) was present in retinas from untreated 12 month of age DBA/2J mice, and was completely prevented in all retinas from nicotinamide-treated DBA/2J mice. GCL=ganglion cell layer (retinal ganglion cell bodies), IPL=inner plexiform layer (retinal ganglion cell dendrites and synapses). Haematoxylin (dark blue/purple) is a general marker of cell nuclei used as a counter-stain.

Figure 8:
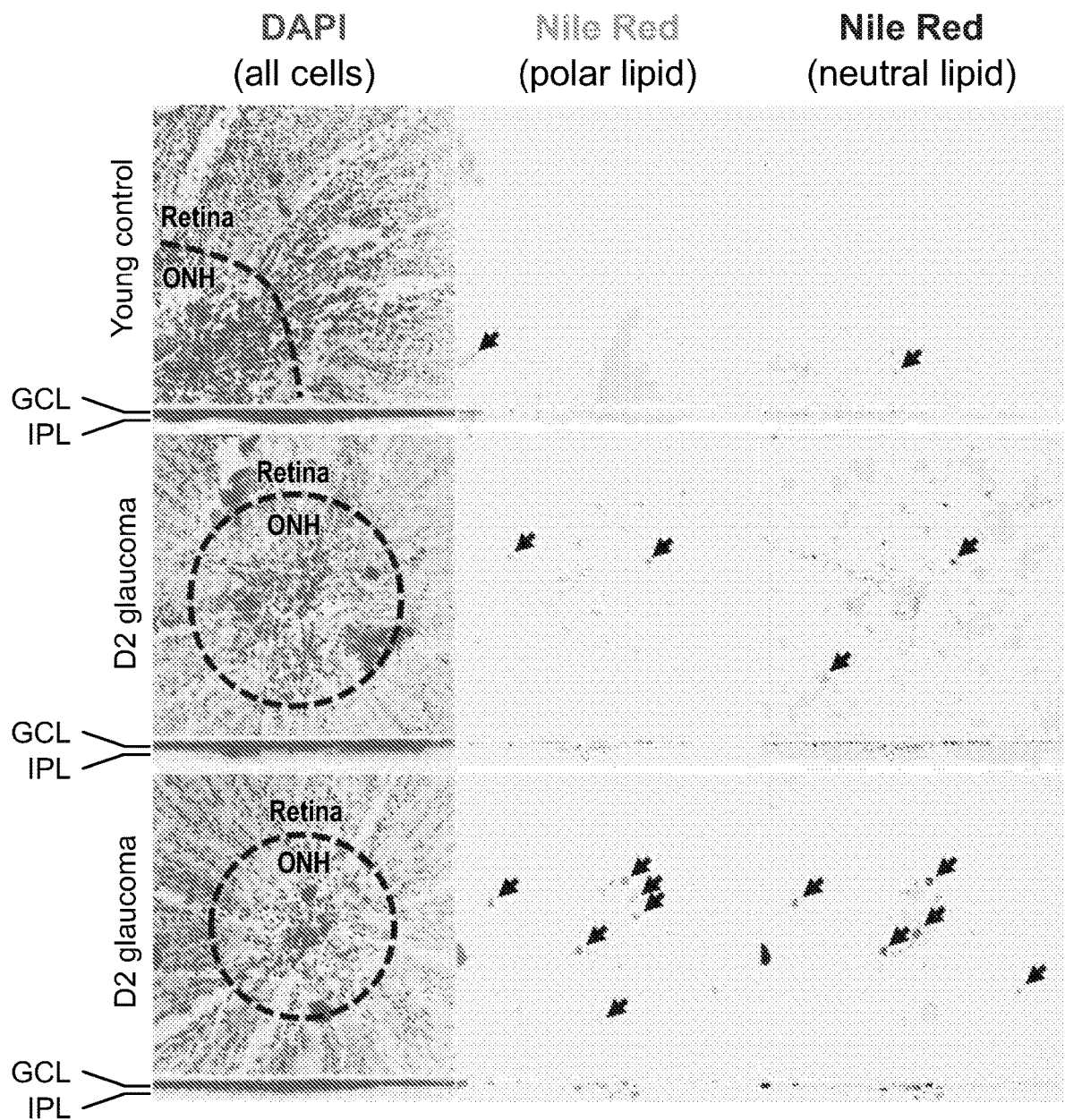

FIG. 8 shows in vivo labeling of lipid droplets detects eyes with early glaucoma. Top row: Young D2 mice that have yet to develop elevated IOP and did not have detectable lipid droplets by typical histology were used as controls. Nile Red staining was mostly absent throughout the retina and optic nerve head (ONH) with some small superficial lipid present in the ganglion cell layer (GCL). Top image represents a top-down/bird's eye view of the retina. Lower image represents an optical cross section of the retina showing the GCL and IPL (inner plexiform layer). Dotted line demarcates the border between the retina and the ONH. Center and bottom row: Two examples of 10.5 month of age D2 mice detected to have glaucoma. This example shown center has early glaucoma, whereas the example shown bottom has developed a more severe glaucoma (based on the lower cell density in the GCL). Nile Red stained droplets were present across the retina but were most abundant in the ONH (which is a site of considerable metabolic stress). Lipid droplets were present in both in the GCL (where the retinal ganglion cell bodies are located) and the IPL (where the retinal ganglion cell dendritic and synaptic processes are located). Nile Red positive lipid droplets were as big as 20 μm in diameter in these samples and their size distribution and locations matched those seen in histologic sections. In the more severely affected eye the lipid droplets tended to be larger and more intensely stained.

Figures provided herein are intended to help illustrate the invention or assist with developing an understanding of the invention, and are not intended to be definitions of the invention's scope.

DETAILED DESCRIPTION OF THE INVENTION

Definitions

The terms used in this application shall have the following meanings.

As used herein, the term "glaucoma" refers to an eye disease that results in damage to the retina and optic nerve and visual dysfunction or vision loss. Glaucoma occurs more commonly among older people. Vision loss from glaucoma is permanent and is irreversible. The term "glaucoma" used herein is intended to encompass primary open angle glaucoma, secondary open angle glaucoma, normal tension glaucoma, hypersecretion glaucoma, primary angle-closure glaucoma, secondary angle-closure glaucoma, plateau iris glaucoma, pigmentary glaucoma, combined-mechanism glaucoma, developmental glaucoma, steroid-induced glaucoma, exfoliation glaucoma, amyloid glaucoma, neovascular glaucoma, malignant glaucoma, capsular glaucoma, plateau iris syndrome, and the like.

As used herein, the term "normal intraocular pressure (normal IOP)" in humans refers to a human subject having an IOP value of 10 mmHg to 21 mmHg. Some individuals, however, may develop optic nerve damage despite having a normal IOP (known as normal-tension glaucoma).

As used herein, the term "high or elevated intraocular pressure (high IOP)" in humans refers to a human subject having an IOP value greater than or equal to 21 mmHg (or 2.8 kPa). High IOP is known to be a risk factor for glaucoma. Some individuals, however, may have high IOP for years and never develop optic nerve damage.

As used herein, "ocular neurodegeneration" is intended to encompass retinal neurodegeneration and optical nerve neurodegeneration.

As used herein, the term "neuroprotective" or "neuroprotection" refers to the ability to protect neurons, their synapses, dendrites, somas, or axons in the ocular nerve (e.g., optic nerve), central or peripheral nervous system from damage (including functional dysfunction) or death, or to delay the onset of neuronal damage or death, or alleviate the severity of the neuronal damage/extent of death among a population of neurons.

As used herein, the term "preventing" or "prevention" with respect to, for example, neuronal damage or death in general, or ocular neurodegeneration disease (e.g., glaucoma) in particular, refers to the ability of compounds or agents to confer neuroprotection, preferably before such damage, death, or disease occurs. Thus prevention of glaucoma includes avoiding the development of glaucoma, reducing the risk or chance of eventually developing glaucoma, delaying the onset or progression of glaucoma, or reducing the severity of neuronal damage/extent of neuronal death/loss among a population of neurons should glaucoma eventually develop.

As used herein, the term "treating" or "treatment" includes the administration of compounds or agents to a subject to alleviate, arrest, or inhibit development of the symptoms or conditions associated with neurodegeneration, such as glaucoma.

As used herein, "improving vision or visual function" refers to the effect of the compounds or agents of the present invention in improving vision or a visual function (such as a visual field test or pattern electroretinography (PERG) amplitude of RGC) in a subject administered with such compounds or agents, as compared to a control subject not administered with such compounds or agents.

As used herein, the term "therapeutically effective amount" means the amount that, when administered to a subject, produces effects for which it is administered. For example, a "therapeutically effective amount," when administered to a subject to inhibit neurodegeneration, reduced IOP elevation, and/or improves RGC function (e.g., prevents the worsening of RGC function).

As used herein, the terms "subject" and "patient" are used interchangeably and refer to a mammal, such as a rodent, a dog, a non-human mammal, and a human. Accordingly, the term "subject" or "patient" as used herein means any mammalian patient or subject (e.g., human or non-human) to which the methods of the present invention can be used to diagnose, prognose, or monitor glaucoma, or neurodegeneration in glaucoma or elevated IOP.

As used herein, the term "a subject suspected of having retinal and/or optic nerve neurodegeneration" refers to a subject (e.g., a human) who may possibly have neurodegeneration in retina and/or optic nerve, including but not limited to: a subject (e.g., a human) at risk of having retinal and/or optic nerve neurodegeneration, which subject may or may not have exhibited any signs or symptoms of retinal and/or optic nerve neurodegeneration or glaucoma; a subject (e.g., a human) having a high or elevated IOP; a subject (e.g., a human) having fat droplets deposited in retina region or optic nerve region; or a subject (e.g., a human) undergoing an eye exam by an eye doctor, such as a routine annual eye exam, which may encompass a retinal examination to evaluate the condition of the optic nerve.

As used herein, "a subject in need of diagnosing glaucoma" refers to a subject (e.g., a human) who exhibit a symptom consistent of glaucoma; a subject who may or may not have already exhibited signs or symptoms of retinal and/or optic nerve neurodegeneration or glaucoma but seeks diagnosis of glaucoma; a subject who is associated with a risk factor for developing glaucoma, such as a factor selected from the group consisting of: intraocular pressure (IOP), age (e.g., 40 years or older, or 60 years or older), race or ethnic background (e.g., African American), family history, gender, medical condition (diabetes, heart disease, high blood pressure and sickle cell anemia), eye condition (myopia, hyperopia), eye injury or surgery (e.g., after ocular trauma, which can induce glaucoma), early estrogen deficiency, corneal thickness, and corticosteroid medication (e.g., during/after corticosteroid treatment, which induces glaucoma in some individuals, such as those using eye droplets over long period of time). The subject may be one on medications that increase risk of glaucoma. The subject (e.g., a human) may be having a high or elevated IOP. For example, the subject may have IOP above 30 mmHg who are at very high risk of glaucoma; or the subject may have IOP above 20-21 mmHg who are at increased risk of glaucoma; or the subject may have IOP at 16 mmHg or above, as normal tension glaucoma commonly occurs at these levels of IOP. The subject may be one (e.g., a human) undergoing an eye exam, such as a routine annual eye exam, which may encompass a retinal examination to evaluate the condition of the optic nerve.

As used herein, the term "medicament" or "pharmaceutical composition" refers to a pharmaceutical formulation that is of use in treating, improving a symptom, or curing of a disease, or in treating, ameliorating, or alleviating the symptoms of a disease.

The following abbreviations are used for certain pharmaceutical compositions that treats or prevents glaucoma or at least a symptom of glaucoma:

NAMPT—nicotinamide phosphoribosyl transferase
NMNAT—nicotinamide mononucleotide adenylyl transferase
NaMN—nicotinic acid mononucleotide
NR—nicotinamide riboside The term "diagnose" or "diagnosis," as used herein in relation to retinal and/or optic nerve neurodegeneration or glaucoma, refers to a process of determining the presence of retinal and/or optic nerve neurodegeneration or glaucoma, respectively, in a subject. The subject may, but does not need to, have already displayed any signs or symptoms of retinal and/or optic nerve neurodegeneration or glaucoma.

The term "prognose" or "prognosis," as used herein in relation to retinal and/or optic nerve neurodegeneration or glaucoma, refers to a process of predicting a likely outcome of a subject's current standing with respect to retinal and/or optic nerve neurodegeneration or glaucoma.

As used herein, the term "expression vector" refers to a nucleic acid molecule that is capable of effecting expression of a gene/nucleic acid molecule it contains in a cell compatible with such sequences. The expression vectors typically include at least suitable promoter sequences and optionally, transcription termination signals.

As used herein, the term "fat droplet," "oil droplet" and "lipid droplet" are used interchangeably.

Overview

In one aspect, the present invention is partly based on the surprising finding that the lipid droplets are deposited in the retina region and optic nerve region in a glaucoma-prone subject/patient and that such lipid droplets represent an early stage glaucoma process as well as a reliable biomarker for ocular neurodegeneration. Therefore, the presence of oil droplets in retina and optic nerve represents a diagnostic tool for early glaucoma. Furthermore, since the intensity of oil droplet seems to increase as disease progresses, it also represents a good prognosis tool.

Without being bound by a particular theory, the present inventors believe that mitochondria defect in early glaucoma causes a shift in fatty acid metabolism, resulting in lipid droplets deposition in retina and in optic nerve. Thus, the presence of oil droplets in the regions represents a reliable biomarker of dysfunction and stress, and is an independent predictor (with respect to increased IOP, for example) that accurately predicts glaucoma and ocular neurodegeneration. The method of the invention can be used independently, or in conjunction with other traditional diagnostic tools (such as IOP measurement), to detect and monitor glaucoma and ocular neurodegeneration.

The presence of the oil droplets show that abnormalities are already present, and a damaging process is underway. The presence of the oil droplets can occur either prior to or during neural damage. Thus, the presence of the oil droplets can identify individuals who are on the path to neural damage; and importantly, at a very early stage where intervention will be most beneficial before vision is irreversibly lost. The presence of the oil droplets may also aid in diagnosis of existing neural damage at early disease stages that are currently very hard to detect. The presence of the oil droplets can further diagnose individuals in which neural damage is still ongoing despite treatments or those in whom treatments are working well (i.e., allow tailoring of treatment with a new degree of precision and over shorter timeframes than currently possible). The method of the invention is much more sensitive and accurate than traditional approach, such as monitoring IOP alone.

Thus, it is an aspect of the present invention to provide a method of detecting retinal and/or optic nerve neurodegeneration in a subject (e.g., human) with glaucoma or elevated intraocular pressure.

One such method comprises an in vivo screening method comprising a step of detecting the presence and/or amount of fat droplets in the retina (e.g., inner retina) and/or optic nerve of a patient. The patient can be further evaluated upon the detection of the presence of fat droplets in the retina (e.g., inner retina) and/or optic nerve in the patient.

The presence or an increased level of fat droplets is indicative of neurodegeneration in the retinal ganglion cells (RGCs), as well as predictive of the progression of neurodegeneration in the RGCs.

The presence or the level/amount of the fat droplets can also be used to monitor the status and/or progression of neurodegeneration in the RGCs. For example, if the neurodegeneration in the RGCs is treated by administering a compound or therapeutic agent to the subject, the presence or the level/amount of the fat droplets before and after the administration can be compared to monitor the status and/or effectiveness of the treatment.

It is one aspect of the present invention to provide a method for diagnosing ocular (e.g., retinal and/or optic nerve) neurodegeneration in a subject having glaucoma or elevated intraocular pressure, or for diagnosing glaucoma, by detecting the presence and/or amount of fat droplets in the retina (e.g., inner retina) and/or optic nerve of the subject.

It is another aspect of the present invention to provide a method for prognosing ocular (e.g., retinal and/or optic nerve) neurodegeneration in a subject having glaucoma or elevated intraocular pressure, or for prognosing glaucoma, by detecting the presence and/or amount of fat droplets in the retina (e.g., inner retina) and/or optic nerve of the subject.

It is yet another aspect of the present invention to provide a method for monitoring ocular (e.g., retinal and/or optic nerve) neurodegeneration in a subject having glaucoma or elevated intraocular pressure, or for monitoring glaucoma, by detecting the presence and/or amount of fat droplets in the retina (e.g., inner retina) and/or optic nerve of the subject. In certain embodiments, the subject has been, or is being, treated for glaucoma or high IOP.

In certain embodiments, the method comprises the steps of: a) providing a subject suspected of having ocular neurodegeneration; and, b) detecting the presence of fat droplets in a retinal region or optic nerve of said subject, wherein the presence of fat droplets in the retinal region or optic nerve region of said subject is indicative of ocular neurodegeneration.

In certain embodiments, the ocular neurodegeneration is retinal neurodegeneration.

In certain embodiments, the ocular neurodegeneration is optic nerve neurodegeneration.

In certain embodiments, step b) comprises: i) administering a fluorescent dye to the subject; and, ii) detecting the presence of fluorescence in the retinal region and/or optic nerve region of said subject, wherein said presence of fluorescence is indicative of the presence of fat droplets in said retinal region and/or optic nerve region, and wherein said presence of fat droplets in said retinal region and/or optic nerve region of said subject is indicative of retinal and/or optic nerve neurodegeneration.

In certain embodiments, the fluorescent dye is a lipophilic dye, such as Oil Red O, Nile Blue, Nile Red, SRFluor680, LD540, LipidGreen, ICG/indocyanine green, or fluorescent nanoprobe.

In certain embodiments, the fluorescent dye is Nile Red or Indocyanine green (ICG).

In certain embodiments, the subject has glaucoma, has high IOP, has a glaucoma risk factor, and/or has not been known to have developed neural damage in retina.

In certain embodiments, the subject has glaucoma (e.g., early stage glaucoma).

In certain embodiments, the fluorescent dye is introduced into the eye of the subject by intravitreal injection, intravenous injection, topical application, or iontophoresis. In certain embodiments, the fluorescent dye is introduced via diet or drink.

In certain embodiments, the fluorescent dye is introduced into the eye two or more times (e.g., 2, 3, 4, 5, 6, 7, 8, 9, 10 times or more).

In certain embodiments, the fluorescent dye is detected after a set period time post introduction of the fluorescent dye, wherein the set period of time is 3-5 minutes, about 10 minutes, 20-60 minutes, 1-3 hrs, 5-10 hrs, 12-24 hrs, 1 day, 2 days, 3 days, 4 days, 5 days or more.

In certain embodiments, the fluorescent dye is detected in vivo using a non-invasive detection method selected from the group consisting of: Scanning Laser Ophthalmoscopy (SLO), fundoscopy (such as a fluorescent fundal imaging modality), and biomicroscope.

In certain embodiments, the non-invasive detection method is Scanning Laser Ophthalmoscopy (SLO).

In certain embodiments, the fat droplets are detected in a retinal region, such as the inner plexiform layer (IPL) where retinal ganglion cell dendrites and synapses reside.

In certain embodiments, the fat droplets are detected in optic nerve.

In certain embodiments, the fat droplets are detectable by a non-invasive detection method such as fundoscopy, OCT (Optical coherence tomography), Scanning Laser Ophthalmoscopy (SLO), Adaptive Optics SLO (AOSLO), Ramen spectroscopy, or intravascular Ultrasound-guided Photoacoustic imaging of lipid.

In certain embodiments, the fat droplets are detectable by any one of the non-invasive detection method herein, optionally in combination with using one or more fluorescent marker dyes or other agents that highlight the lipid droplets. For example, the fluorescent marker dyes or other agents that highlight the lipid droplets may include, without limitation, a vital lipid stain (such as Oil Red O, Nile Blue, Nile Red, SRFluor680, LD540, LipidGreen, or ICG/indocyanine green), or fluorescent nanoprobe.

The dyes or agents can be introduced into the subject (e.g., a human patient) by injection, such as by i.v. or onto the eye(s) of the patient, e.g., intravitreal injection, or topical application, in order to detect the lipids. The dye may be introduced repeatedly. The dye can be detected after a period of time for optimal detection, such as after a period of 3-5 minutes, about 10 minutes, 20-60 minutes, 1-3 hrs, 5-10 hrs, 12-24 hrs, 1 day, 2 days, 3 days, 4 days, 5 days or more. The dyes may be fluorescent, which may be beneficial for detection by SLO, fundoscopy or other equivalent instruments.

In certain embodiments, the methods of the present invention relate to the detection (e.g., presence or absence) of fat droplets in the retina (e.g., inner retina) and/or optic nerve of the subject.

In certain embodiments, the methods of the present invention relate to the measurement and/or the quantification of the amounts of fat droplets in the retina and/or optic nerve of the subject. In certain embodiments, the amounts of the fat droplets are compared to that of a control, or that of a condition or status before a treatment or therapeutic intervention.

In certain embodiments, the subject has a normal IOP value of <21 mmHg. In other embodiment, the subject has an elevated IOP value of ≥21 mmHg.

In certain embodiments, the subject is an adult human, such as an adult human over age 40, 50, or 60.

In certain embodiments, the subject may have no signs or symptoms of glaucoma or retinal and/or optic nerve neurodegeneration, but is known or suspected to be associated with a risk factor for developing glaucoma or neurodegeneration in glaucoma selected from the group consisting of: intraocular pressure (IOP), age, race or ethnic background, family history, gender, medical condition (diabetes, heart disease, high blood pressure and sickle cell anemia), eye condition (myopia, hyperopia), eye injury or surgery, early estrogen deficiency, corneal thickness, and corticosteroid medication (eye droplets over long period of time).

In certain embodiments, the subject is a patient seeking routine annual eye examination.

In certain embodiments, the method further comprises selecting the subject for receiving treatment for glaucoma when the retinal region and/or optic nerve is found to have fat droplets.

In certain embodiments, the treatment comprises administering to the subject a therapeutically effective amount of a composition comprising an agent selected from the group consisting of: nicotinamide (NAM), nicotinamide mononucleotide (NMN), nicotinamide adenine dinucleotide (NAD), pyruvate, Pyrroloquinoline Quinone (PQQ), and a combination thereof, thereby treating glaucoma.

In certain embodiments, the treatment comprises the step of administering a gene composition, wherein the gene composition comprising a polynucleotide encoding nmnat1.

In certain embodiments, the treatment further comprises administering to the subject an additional therapeutic agent selected from the group consisting of: a beta blocker, a nonselective adrenergic agonist, a selective α-2 adrenergic agonist, a Carbonic Anhydrase Inhibitor (CAI), a prostaglandin analog, a parasympathomimetic agonist, a carbachol or a combination thereof.

Another aspect of the present invention is to provide a method of determining glaucoma risk by detecting the presence and/or amounts of fat droplets in the retina (e.g., inner retina) and/or optic nerve of the subject. In one embodiment, the risk is determined by measurement of an increased or elevated expression or level of fat droplets relative to a control level (e.g., determined statistically or via normalization). The increased expression of fat droplets correlates with an increased risk for neurodegeneration, due to glaucoma or to elevated intraocular pressure.

Another aspect of the present invention is to provide a method for identifying compounds for the treatment of neurodegeneration in glaucoma or in elevated intraocular pressure. Such compounds are identified, in certain embodiments, according to one or more of the screening methods detailed above. In general, compounds identified according to the screening methods are modulators of fat droplets in the retina of a subject.

Thus this aspect of the present invention provides a method for identifying a compound for the treatment of neurodegeneration and/or elevated intraocular pressure in glaucoma, the method comprising the steps of: a) providing a candidate compound; b) administering the candidate compound to a subject having neurodegeneration and/or elevated intraocular pressure; c) detecting the presence and optionally the amount of fat droplets in a retinal region and/or optic nerve of the subject; wherein the absence, or a decrease of the amount, of fat droplets in the retinal region and/or optic nerve of the subject after administering the candidate compound, as compared to a control subject not administered the candidate compound, identifies the candidate compound as being the compound for the treatment of neurodegeneration and/or elevated intraocular pressure in glaucoma.

In certain embodiments, the subject is a DBA/2J mouse.

In certain embodiments, the presence or absence, or the amount of the fat droplets, is determined by fundoscopy, OCT (Optical coherence tomography), Scanning Laser Ophthalmoscopy (SLO), Adaptive Optics SLO (AOSLO), or Ramen spectroscopy, optionally in combination with using one or more fluorescent marker dyes or other agents that highlight the lipid droplets.

In certain embodiments, the presence or absence, or the amount of the fat droplets, is determined via a biopsy obtained from the retina region and/or optic nerve.

Another aspect of the present invention is to provide a method of screening compounds for use as therapies for neurodegeneration in glaucoma or in elevated intraocular pressure. One such method comprises an in vivo screening method further comprising a step of administering a test compound to a subject. The test compound may be a compound that has been identified by the screening method as being potentially useful as therapies for neurodegeneration in glaucoma or in elevated intraocular pressure.

Thus this aspect of the present invention provides a method for screening for a compound for use as a therapeutic agent to treat neurodegeneration in glaucoma or to treat elevated intraocular pressure, the method comprising the steps of: a) providing a candidate compound; b) administering the candidate compound to a subject having neurodegeneration in glaucoma and/or elevated intraocular pressure; c) detecting the presence and optionally the amount of fat droplets in a retinal region and/or optic nerve of the subject; wherein the absence, or a decrease of the amount, of fat droplets in the retinal region and/or optic nerve of the subject after administering the candidate compound, as compared to a control subject not administered the candidate compound, identifies the candidate compound as being the compound for use as the therapeutic agent to treat neurodegeneration in glaucoma or to treat elevated intraocular pressure.

Detection of fat droplets can be conveniently performed using techniques known to those of skill in the art. In certain embodiments, the presence of fat droplets is determined via a non-invasive detection method, such as fundoscopy, OCT (Optical coherence tomography), Scanning Laser Ophthalmoscopy (SLO), Adaptive Optics SLO (AOSLO), or Ramen spectroscopy, optionally in combination with using one or more fluorescent marker dyes or other agents that highlight the lipid droplets.

In another embodiment, the presence of fat droplets is determined via a biopsy obtained from retina. Biological samples used with embodiments of the present invention may be ocular tissue containing retina. Biological samples may be processed disclosed herein or known to those of skill in the art. Processing may include fixing and methods known to those of skill in the art. Fat droplets can be conveniently stained with a dye, such as Oil Red O.

With the inventions generally described above, the following sections provide more detailed descriptions for further aspects of the invention.

Non-Invasive Detection of Fat Droplets

It is an aspect of the present invention to provide a non-invasive medical imaging procedure to detect lipid droplets in the retina in humans. Several medical procedures are conveniently available to detect the presence of lipid droplets in the retina in humans. For example, Fundoscopy (aka ophthalmoscopy) is a medical procedure that allows physician to view the retina through a dilated pupil in humans. The procedure is routinely performed in a clinic, typically using a hand-held ophthalmoscope. This allows the examining of the health of the vitreous, retina, and optic disc where retinal ganglion cell axons exit the eye and become the optic nerve; also know as the "blind spot."

I. Scanning Laser Ophthalmoscopy

Scanning Laser Ophthalmoscopy (SLO) or Adaptive Optics SLO (AOSLO) is a more advanced/higher resolution version of the typical ophthalmoscope that uses confocal scanning laser microscopy to image the retina. At this resolution, a physician can image lipid build-ups in the posterior eye cup (i.e., retina, optic disc) that are common in conditions such as age-related macular degeneration, and diabetic retinopathy.

In AMD these are called drusen and are protein/lipid deposits that range from smaller/undetectable to >125 µm in diameter. In diabetes, lipid leakage from surrounding capillaries forms yellow flecks in the retina called exudates. Exudates can either be "hard" (punctate and small in size) or "soft" (larger in size, often called cotton-wool exudates. They are both lipid and cytoid bodies (swollen nerve fibers).

SLO can be expanded to include fluorescein angiographic and auto-fluorescence images that allow higher resolution images of retinal blood vessel and auto-fluorescence particles in the retina. Auto-fluorescence in the retina can also be used to identify lipid particles and immune cells.

In certain embodiments, the method comprises administering to the patient a vital lipid stain (such as Oil Red O, Nile Blue, Nile Red, SRFluor680 (commercially available), monodansylpentane (MDH), LD540, LipidGreen, or ICG/indocyanine green) by injection, such as by i.v. or onto the eye(s) of the patient, e.g., intravitreal injection, in order to detect the lipids. The dyes may be fluorescent, which may be beneficial for detection by SLO or fundoscopy.

For example, Oil Red O (also known as Solvent Red 27, Sudan Red 5B, C.I. 26125, $C_{26}H_{24}N_4O$) is a lysochrome (fat-soluble dye) diazo dye that has been used for staining neutral triglycerides and lipids on frozen sections and some lipoproteins on paraffin sections. It has the appearance of a red powder with maximum absorption at 518 (359)nm. Other similar dyes that may be used include Sudan III, Sudan IV, and Sudan Black B.

Nile Red (also known as Nile Blue oxazone) is a lipophilic stain that stains intracellular lipid droplets yellow. In most polar solvents, Nile Red will not fluoresce. However, when in a lipid-rich environment, it becomes intensely fluorescent, with varying colors from deep red (for polar lipid) to strong yellow-gold emission (for neutral lipid in intracellular storages). See Greenspan et al. (Nile Red: a selective fluorescent stain for intracellular lipid droplets, *J Cell Biol.* 100(3): 965-973, 1985); Bonilla and Prelle (Application of Nile Blue and Nile Red, two fluorescent probes, for detection of lipid droplets in human skeletal muscle, *J Histochem Cytochem.* 35(5): 619-621, 1987).

PEG-PLA coated Nile Red particles have been shown to have fast clearance in vivo (Schadlich et al., *Pharm. Res.* 28: 1995-2007, 2011). Thus it may be safely administered in vivo by IV infusion.

Rice et al. (*J Mater Chem B Mater Biol Med.* 3(9):1979-1989, 2015) has used a micellar formulation of the commercially available deep-red fluorescent probe SRFluor680 in non-invasive optical imaging of interscapular brown adipose tissue in mice. SRFluor680 is a lipophilic and uncharged squaraine rotaxane probe that exhibits extremely bright, deep-red fluorescence that enables high-sensitivity in vivo optical imaging. Cell microscopy studies have previously shown that SRFluor680 partitions rapidly and irreversibly into lipophilic intracellular sites such as lipid droplets and the endoplasmic reticulum. SRFluor680 is commercially available (Molecular Targeting Technologies Inc), or it can be synthesized.

In another example, indocyanine green (ICG) is a Food and Drug Administration (FDA)-approved fluorescence agent safe for in vivo use in, for example, tumor imaging (Kosaka et al., Int. J. Cancer, 129: 1671-1677, 2011; Ishizawa et al., Cancer, 115: 2491-2504, 2009; Vinegoni et al., *Sci Transl Med.* 3(84):84ra45, 2011).

Monodansylpentane (MDH) is a high contrast blue-fluorescent marker for lipid droplets (LDs). The unique spectral properties make MDH easily combinable with other green and red fluorescent reporters for multicolor fluorescence imaging. MDH staining does not apparently affect LD trafficking, and the dye is extraordinarily photo-stable. MDH represents a reliable tool to use for the investigation of dynamic LD regulation within living cells using fluorescence microscopy. See Yang et al., Monodansylpentane as a Blue-Fluorescent Lipid-Droplet Marker for Multi-Color Live-Cell Imaging, PLOS One, doi.org/10.1371/journal.pone.0032693, 2012.

LD540 is a lipophilic dye based on the Bodipy fluorophore, and was developed for microscopic imaging of lipid droplets. It can spectrally be resolved from both green and red fluorophores, allowing multicolor imaging in both fixed and living cells. It supports live cell imaging. See Spandl et al., Traffic. 10(11):1579-84, 2009.

LipidGreen is a small molecule probe for in vivo lipid imaging. LipidGreen stained lipid droplets in 3T3L1 cell lines and fat deposits in zebrafish without apparent toxicity up to 100 µM. See Lee et al., Chem Commun (Camb). 47(26):7500-2, 2011.

II. Optical Coherence Tomography

Optical coherence tomography (OCT, ultra-high resolution OCT; UHT-OCT) is an imaging technique that provides high resolution (to the micrometer), 3D images from scattering (i.e., biological) material. OCT using a long-wavelength light (such as near infrared) that penetrates deeper into tissue than confocal microscopy. OCT is commonly used in the clinic, and is found in most hospitals and large "high-street" optometrists. OCT allows the scanning of the retina at a high resolution, at a current (common) axial resolution of 3 µm and lateral resolution of 4 µm. In comparison, the lipid droplets are up to 30 µm in diameter, and are often 5-10 µm in diameter. OCT is non-invasive and only requires the patient to have their eyes dilated. A typical scan takes 5-10 minutes in the clinic. During research applications, higher resolution scans can take longer, but typically will be less than 20-30 minutes. OCT is commonly utilized to readily image retinal lipid deposits (such as drusen in AMD) at a higher resolution.

III. Ramen Spectroscopy

Raman spectroscopy is a spectroscopic technique used to observe vibrational, rotational, and other low-frequency modes in a system. It relies on inelastic scattering, or Raman scattering, of monochromatic light, usually from a laser in the visible, near infrared, or near ultraviolet range. The laser light interacts with molecular vibrations, phonons or other excitations in the system, resulting in the energy of the laser photons being shifted up or down. The shift in energy gives information about the vibrational modes in the system.

Typically, a sample is illuminated with a laser beam. Electromagnetic radiation from the illuminated spot is collected with a lens and sent through a monochromator. Elastic scattered radiation at the wavelength corresponding to the laser line (Rayleigh scattering) is filtered out by either a notch filter, edge pass filter, or a band pass filter, while the rest of the collected light is dispersed onto a detector.

Any Raman spectroscopy, especially the advanced types of Raman spectroscopy include surface-enhanced Raman, resonance Raman, tip-enhanced Raman, polarized Raman, stimulated Raman (analogous to stimulated emission), transmission Raman, Spatially offset Raman spectroscopy (SORS), and hyper Raman, can be used in the methods of the invention.

Raman spectroscopy has been used as a noninvasive technique for real-time, in situ biochemical characterization of biological tissues such as wounds. Spatially offset Raman spectroscopy (SORS), which is less sensitive to surface layers than conventional Raman, can be used to non-invasively study biological tissue. A huge reason why Raman spectroscopy is so useful in biological applications is because its results often do not face interference from water molecules, due to the fact that they have permanent dipole moments, and as a result, the Raman scattering cannot be picked up on. This is a large advantage specifically in biological applications.

For example, a three-dimensional multiphoton vibrational imaging technique based on stimulated Raman scattering (SRS) has been used in a variety of biomedical applications, such as differentiating distributions of omega-3 fatty acids and saturated lipids in living cells, imaging of brain and skin tissues based on intrinsic lipid contrast, and monitoring drug delivery through the epidermis (Freudiger et al., Science 322(5909): 1857-1861, 2008). The sensitivity of SRS imaging is significantly greater than that of spontaneous Raman microscopy, which is achieved by implementing high-frequency (megahertz) phase-sensitive detection. SRS microscopy has a major advantage over coherent Raman techniques in that it offers background-free and readily interpretable chemical contrast.

Other imaging techniques may also be used in the method of the invention. For example, in vivo intravascular Ultrasound-guided Photoacoustic imaging of lipid has been used to image plaques in an animal model of atherosclerosis. See Wang et al (Ultrasound in Medicine and Biology, 38(12): 2098-2103, 2012). Merian et al. (Fluorescent nanoprobes dedicated to in vivo imaging: from preclinical validations to clinical translation. Molecules. 17(5):5564-91, 2012) have reviewed a wide range of fluorescent nanoprobes designed and tested in preclinical studies. In comparison to low-molecular weight organic dyes, the use of fluorescent nanoprobes can improve both the signal sensitivity (better in vivo optical properties) and the fluorescence biodistribution (passive "nano" uptake in tumors for instance), and thus such fluorescent nanoprobes (all incorporated herein by reference) can also be used in the methods of the invention.

To the best of inventors' knowledge, our finding of accumulation of lipid droplets in retina preceding glaucoma represents the first report in this area. The present invention further provides a method of utilizing the lipid droplet accumulation as a diagnostic biomarker for the detection and monitoring of the progress of glaucomatous neurodegeneration. The common clinical imaging modalities can be easily applicable to become a useful diagnostic tool via identifying and quantifying lipid deposits in the retina of patients with glaucoma. Given the present finding that lipid accumulation is a prominent component in glaucoma-prone eyes, the present invention provides the use of Scanning Laser Ophthalmoscopy and Optical coherence tomography as a viable diagnostic to determining pre-glaucomatous changes in the human retina. The present invention provides a reliable and accurate diagnostic test and thereby offers early therapeutic intervention in human glaucoma diseases.

DBA/2J Mouse Model

The present inventors chose to use of DBA/2J (D2) mouse model because this mouse strain develops an inherited age-related glaucoma that highly mimics human glaucoma. D2 mice are one of the most studied models of glaucoma with many established similarities to human glaucoma, including induction of the same disease mediating molecules (for example complement component molecules), the same location of a key glaucoma insult in the optic nerve head, and the same topographical pattern of RGC death as occurs in human glaucoma. The D2 mice have iris disease and high intraocular pressure starting at about 6 months of age. By 9 months of age, high ocular pressure has been ongoing in the eyes of the majority of the D2 mice. At about the same time, fat droplet deposits in inner retina began to be seen. The D2 mice subsequently have a progressive vision loss, optic nerve damage, and inner retina dysfunction. At 12 months of age, when designed experiments typically end, ~70% of the D2 mice eyes have a severe disease based on histological examination of the retina and optic nerve. At this stage, fat droplet deposits are widely seen in most D2 mice eyes.

Topical administration of compounds (e.g., memantine, timolol, or Latanoprost) lowers IOP in D2 mice and reduces the risk of developing neurodegeneration as they do in human glaucoma. Control D2-Gpnmb$^+$ is an age- and strain-matched mouse that does not develop glaucoma.

Ocular Pressure in Glaucoma

Intraocular pressure (IOP) can be determined using, for example, Goldmann applanation tonometry (Haag Streit, Bern, Switzerland). In humans, normal IOP is 12-21 mmHg. IOP that exceeds 21 mmHg is considered high. Elevated IOP is a major risk factor in glaucoma. Of those with POAG (primary open angle glaucoma, the most common glaucoma accounting for >90% of cases), 25 mmHg is the median untreated baseline IOP.

The Baltimore eye study (www.ncbi.nlm.nih.gov/pub/12049574) reported that high risk=IOP>25.75 mmHg; moderate risk=IOP 23.75-25.75 mmHg; and low risk=IOP <23.75 mmHg. Lowering IOP by 20% to a level below 24 mmHg decreases risk of progression from 9.5% to 4.4% at 5 years. The chance of blindness in 1 eye is 27% after 10 years post diagnosis, and 38.1% after 20 years. The chance of blindness in both eyes is 6% and 13.5% respectably.

In human glaucoma patients, such as primary open agent glaucoma (POAG) patients, glaucoma is asynchronous and age-related (most commonly occurring at >40 years old). Untreated glaucoma takes on, average, 14 years to progress from early to late stage disease when IOP is 21-25 mmHg. This rate of progression rapidly increases as IOP increases (~3 years to progress from early to late stage disease when IOP >30 mmHg).

In human patients, treatments that lower IOP (surgical or pharmacological) reduce the risk of developing neurodegeneration. The rates of disease progression and percentage chance of going blind are likely misrepresented due to patients not being diagnosed. It is generally believed that high IOP does not always indicate glaucoma (~30% blind after 10 years, ~40% after 20). Lowering IOP does not cure glaucoma, but does reduce the risk factor by 58%. Despite the conventional IOP lowering preventions, there is still a risk of vision loss, and even blindness. There are limited available neuroprotective strategies in glaucoma. Vision loss in glaucoma is irreversible. In fact, glaucoma is the leading case of irreversible blindness in the world.

Retinal Ganglion Cells (RGCs)

Retinal ganglion cells (RGCs) are the output neuron of the retina. They receive visual information from the photoreceptors (i.e., rods and cones) via intermediate neurons (i.e., bipolar cells and amacrine cells). This visual information starts as the photons in light, and culminates in an electric potential at retinal ganglion cell synapses. RGCs have long axons that leave the cell body and traverse across the retina to the optic disc (i.e., blind spot) where they exit out of the eye (optic nerve head). Just beyond the optic nerve head (myelin transition zone), retinal ganglion cell axons become myelinated and form the optic nerve (i.e. the optic nerve is a bundle of retinal ganglion cell axons, in the mouse this is ~50,000 depending on the strain). Axons in the optic nerve eventually reach terminal visual centers in the brain that then relay these signals on or process this information themselves. Two important visual centers that retinal ganglion cell axons terminate in are the lateral geniculate nucleus (LGN) and the superior colliculus (sup. col./SC).

Retinal ganglion cells are specifically affected (i.e., cell loss) in glaucoma. Damage to the RGCs likely occurs at the axon at the site of optic nerve head. It is speculated that because of the stress induced on the eye by abnormally high IOP, the optic nerve head is a "weak spot" in the eye where mechanical insults to the retinal ganglion cell axon may occur. The axon is not the only point of insult in the retinal ganglion cell, as pressure throughout the eye also must affect the soma and dendrites as well. The exact underlying mechanism of how RGCs damage is not totally clear.

In the DBA/2J (D2) mice, the present inventors showed that at time-points where IOP is high, there is no detectable axon loss in the optic nerve (i.e., no ocular neurodegeneration). Surprisingly, the present inventors discovered that there are early mitochondrial and molecular changes, dendrite atrophy, and synaptic loss.

The present inventors further discovered that, among the early defects, prior to ocular neurodegeneration, is the phenomenon of fat droplets deposit in the inner retina of D2 mice (most prominently in the inner plexiform layer (IPL) where retinal ganglion cell dendrites and synapses reside) that will eventually develop retinal and/or optic nerve neurodegeneration in this mouse model of glaucoma. As the disease and neurodegeneration progress, the prevalence, extent, and amount of the fat droplets also increases.

These findings indicate that the effects of IOP manifest in other compartments of the retinal ganglion cell, not just the axon in the optic nerve.

Neurodegeneration Treatment

The methods of the present invention can be used to diagnose or prognose glaucoma or retinal and/or optic nerve neurodegeneration in glaucoma or high IOP. A subject diagnosed to have glaucoma or retinal and/or optic nerve neurodegeneration in glaucoma or high IOP, or diagnosed to have a high risk of developing glaucoma or retinal and/or optic nerve neurodegeneration in glaucoma or high IOP, may be treated by agents useful for treating glaucoma or retinal and/or optic nerve neurodegeneration in glaucoma or high IOP.

The methods of the present invention can also be used to monitor the status or efficacy of neurodegeneration treatment.

A number of agents have been identified as being effective to treat glaucoma, and/or retinal and/or optic nerve neurodegeneration in glaucoma or high IOP.

In certain embodiments, the agent comprises a nicotinamide adenine dinucleotide (NAD$^+$) precursor (e.g., nicotinic acid, nicotinamide (NAM), nicotinamide mononucleotide (NMN), nicotinamide riboside (NR), or a combination thereof), a Krebs Cycle intermediate or precursor thereof (e.g., pyruvate), or a combination thereof.

In certain embodiments, the agent comprises a nicotinamide adenine dinucleotide (NAD$^+$) precursor, e.g., nicotinic acid, nicotinamide (NAM), nicotinamide mononucleotide, nicotinamide riboside, or a combination thereof. In certain embodiments, the NAD$^+$ precursor is nicotinamide or nicotinamide riboside.

Nicotinic acid (also known as niacin, nicotinate, vitamin B3, and vitamin PP) is a vitamin. Its corresponding amide is called nicotinamide or niacinamide. These vitamins are not directly interconvertable.

NAD$^+$ precursor includes nicotinic acid, nicotinamide, nicotinamide riboside, etc., as well as salts thereof, and analogs thereof. In certain embodiments, administering the NAD$^+$ precursor leads to increased intracellular level of NADt (total NAD).

In certain embodiments, the agent comprises a Krebs Cycle intermediate or precursor thereof, or a combination thereof. For example, the Krebs cycle intermediate or precursor is Oxaloacetate, Acetyl CoA, Citrate, CoA-SH, cis-Aconitate, D-Isocitrate, NAD$^+$, Oxalo succinate, NADH, α-Ketoglutarate, Succinyl-CoA, GDP, ubiquinone, Succinate, Fumarate, L-Malate, pyruvate, a monosaccharide (such as glucose, galactose, fructose), a disaccharide (such as sucrose, maltose, lactose), or a combination thereof.

In certain embodiments, the agent is formulated in a pharmaceutical composition that includes nicotinic acid and/or nicotinamide riboside and/or nicotinamide and/or nicotinic acid metabolites. The nicotinic acid and/or nicotinamide riboside and/or nicotinamide and/or nicotinic acid metabolites can be used in free form. The term "free," as used herein in reference to a component, indicates that the component is not incorporated into a larger molecular complex. In some embodiments, the nicotinic acid can be comprised in niacin. The nicotinic acid and/or nicotinamide riboside and/or nicotinamide and/or nicotinic acid metabolites can be in a salt form.

In some embodiments, any of the compositions described herein can include salts, derivatives, metabolites, catabolites, anabolites, precursors, and analogs thereof. For example, the metabolites can include nicotinyl CoA, nicotinuric acid, nicotinate mononucleotide, nicotinate adenine dinucleotide, or nicotinamide adenine dinucleotide. In some embodiments, the compositions comprise nicotinamide. In some embodiments, the compositions can be substantially free of nicotinic acid metabolites.

In certain embodiments, a salt is selected from the group consisting of fluoride, chloride, bromide, iodide, formate, acetate, ascorbate, benzoate, carbonate, citrate, carbamate, formate, gluconate, lactate, methyl bromide, methyl sulfate, nitrate, phosphate, diphosphate, succinate, sulfate, and trifluoroacetate salt.

NAM/nicotinic acid analogs may also be used for treatment. Suitable analogues of nicotinic acid include, for example, isonicotinamide and N-methyl-nicotinamide.

In certain embodiments, keto-, ethyl-, benzyl-, or other non-salt embodiments of NAM can also be used in the instant invention.

The toxicity of NAM/nicotinamide/NAD/NR/pyruvate is low, and relatively large amounts may be administered without toxic effect.

In mice, NAM/nicotinamide/NAD/NR/pyruvate can be administered with a daily dosage of about 200-1,000 mg/kg/day to provide a neuroprotective effect. Preferably, the daily dosage is about 400-600 mg/kg/day. More preferably, the daily dosage is about 550 mg/kg/day. At these dosages, the compounds afford a neuroprotective effect.

In mice, NAM/nicotinamide/NAD/NR/pyruvate can be administered at a dose of about 1,000-5,000 mg/kg/day to provide an IOP lowering effect. Preferably, the daily dosage is about 1,500-3,000 mg/kg/day. More preferably, the daily dosage is about 2,000 mg/kg/day. At these dosages, the compounds afford an IOP lowering effect.

With regard to PQQ, it is tolerated at least at 2,000 mg/kg/day in mice. The neuroprotective effect provided by PQQ is about 20-2,000 mg/kg/day, about 100-1,000 mg/kg/day, or about 500 mg/kg/day in mice.

In humans (~60 kg individuals), NAM/nicotinamide/NAD/NR/pyruvate can be administered at a daily dosage of 0.5-10 grams to provide a neuroprotective effect. Preferably, the daily dosage is about 1-5 grams/day. Preferably, the daily dosage is about 2-4 grams/day. More preferably, the daily dosage is about 2.5 grams/day. At these dosages, the compounds afford a neuroprotective effect.

In humans (~60 kg individuals), NAM/nicotinamide/NAD/NR/pyruvate can be administered at a daily dosage of about 5-25 grams/day to provide an IOP lowering effect. Preferably, the daily dosage is about 10-20 grams/day. Preferably, the daily dosage is about 8-15 grams/day. More preferably, the daily dosage is about 10 grams/day. At these dosages, the compounds afford an IOP lowering effect.

In humans (~60 kg individuals), PQQ can be administered at a daily dosage of about 2-160 mg/kg/day, or about 10-100 mg/kg/day, or about 50 mg/kg/day to afford a neuroprotective effect. In certain embodiments, PQQ can be administered at a daily dosage of ~10 mg-10 g a day, about 50 mg-1 g a day, or about 500 mg a day.

Ideally, typical dosing may be once, twice or three times a day. Total daily dose may be administered once, or administered as two or three separate doses (e.g., with each dose being ½ or ⅓ of the daily total). For multiple dosing, each dose can be the same amount or different amounts. The pharmaceutical composition may be administered in the morning or evening. The pharmaceutical composition may be taken with or without meals.

In certain embodiments, the treatment comprises an additional therapeutic agent for treating glaucoma that includes, but not limited to an agent that lowers IOP. Exemplary additional therapeutic agent includes, but not limited to a beta blocker (such as Timolol maleate, Timolol hemihydrate, Levobunolol HCL, Metipranolol Carteolol, Betaxolol and the like), a non-selective adrenergic agonist (such as Epinepherine, Dipivefrin HCL), a selective α-2 adrenergic agonists (such as Apraclonidine HCL, Brimonidine tartrate, and Brimonidine tartrate in Purite), or a Carbonic Anhydrase Inhibitor (CAI, such as acetazolamide (oral), acetazolamide (parenteral), methazolamide (oral), dorzolamide (topical), and brinzolamide (topical)).

In certain embodiments, the additional therapeutic agent includes a prostaglandin analog (such as Latanoprost, Travaprost, and Bimataprost (prostamide)), a parasympathomimetic agonist (including direct cholinergic agonist such as pilocarpine HCL; and indirect cholinergic agents such as echothiophate iodide, demercarium iodide, and physostigmine isofluorophate), and carbachol (a mixed direct agonist/acetylcholine releasing agent).

In certain embodiment, the additional therapeutic agent comprises a fixed combination medication that offers the potential advantage of increased convenience, compliance, efficacy, and cost. The fixed-combination may comprise a topical beta-blocker combined with a prostaglandin analogue, an alpha-adrenoceptor agonist, or a topical carbonic anhydrase inhibitor. Exemplary fixed combination include: (1) dorzolamide and timolol, such as Dorzolamide hydrochloride 2% and timolol maleate ophthalmic solution 0.5% (e.g., Cosopt, now available as generic), (2) brimonidine with timolol or brinzolamide, such as brimonidine tartrate 0.2%, timolol maleate ophthalmic solution 0.5% (e.g., Combigan) and brimonidine tartrate 0.2% and brinzolamide 1% (e.g., Simbrinza), or (3) latanoprost and timolol.

In certain embodiment, the additional therapeutic agent comprises a hyperosmotic agent such as oral glycerine, oral isosorbide, and intravenous mannitol that can rapidly lower IOP by decreasing vitreous volume. They do not cross the blood-ocular barrier and therefore exert oncotic pressure that dehydrates the vitreous. The hyperosmotic agent is typically used in acute situations to temporarily reduce high IOP until more definitive treatments can be rendered.

In certain embodiments, the treatment is gene therapy for treating retinal and/or optic nerve neurodegeneration in glaucoma, by replacing copies of dysfunctional genes to the eye through introducing exogenous genes into the eye using viral vector-mediated gene delivery.

In certain embodiments, the viral vector includes a vector based on adenovirus, or adeno-associated virus (AAV). In a preferred embodiment, the AAV is AAV2.2. For purposes of this application, it is intended to encompass other AAV serotypes including AAV1, AAV2, AAV4, AAV5, AAV8, AAV9, and the like. In other embodiments, the vector is a Lentivirus, typically a pseudotype HIV-based vector.

To deliver genes targeting RGCs, viral vectors are introduced to the vitreal chamber. In a preferred embodiment, gene delivery is targeted directly proximal to the inner retina. Intravitreal injections are routinely practiced in ophthalmic surgery and can be performed safely in an office/clinic location.

In one aspect, the gene therapy delivers a gene to an eye to increase the expression of Nmnat. In certain embodiments, the gene that increases protein expression of Nmnat includes Nmnat-1, Nmnat-2, or Nmnat-3. In certain embodiments, the gene is Nmnat-1 (e.g., human NMNAT1).

EXAMPLES

The present invention is further illustrated by the following examples and results, and is not to be limited in scope by the specific embodiments disclosed. Those skilled in the art will know, or be able to ascertain using no more than routine experimentation, many equivalents to the specific embodiments of the invention described herein.

Example 1 DBA/2J Mice Have a Progressive Iris Disease that Closely Resembles Human Pigmentary Dispersion The DBA/2J (D2) mouse displays many of the hallmark features of human glaucoma. In the D2 mouse, mutations in two genes (Gpnmb$^{R150X}$ and Tyrp1$^b$) cause a front-of-the-eye disease that closely resembles human pigmentary dispersion and iris atrophy disease, which cause glaucoma. In the eyes of D2 mice, dispersed iris pigments block channels known as trabecular meshwork in the anterior chamber of the eyes. The trabecular meshwork is responsible for the normal homeostasis of aqueous humor production and outflow. As a consequence of its blockage, aqueous humor builds up, increasing the intraocular pressure in the eyes of D2 mice.

Iris disease in D2 eyes is age-related and asynchronous. In our colony used in this experiment, we used 4-month-old D2 mice at a time point where no disease had occurred (FIGS. 1A-1C).

Figure 1:
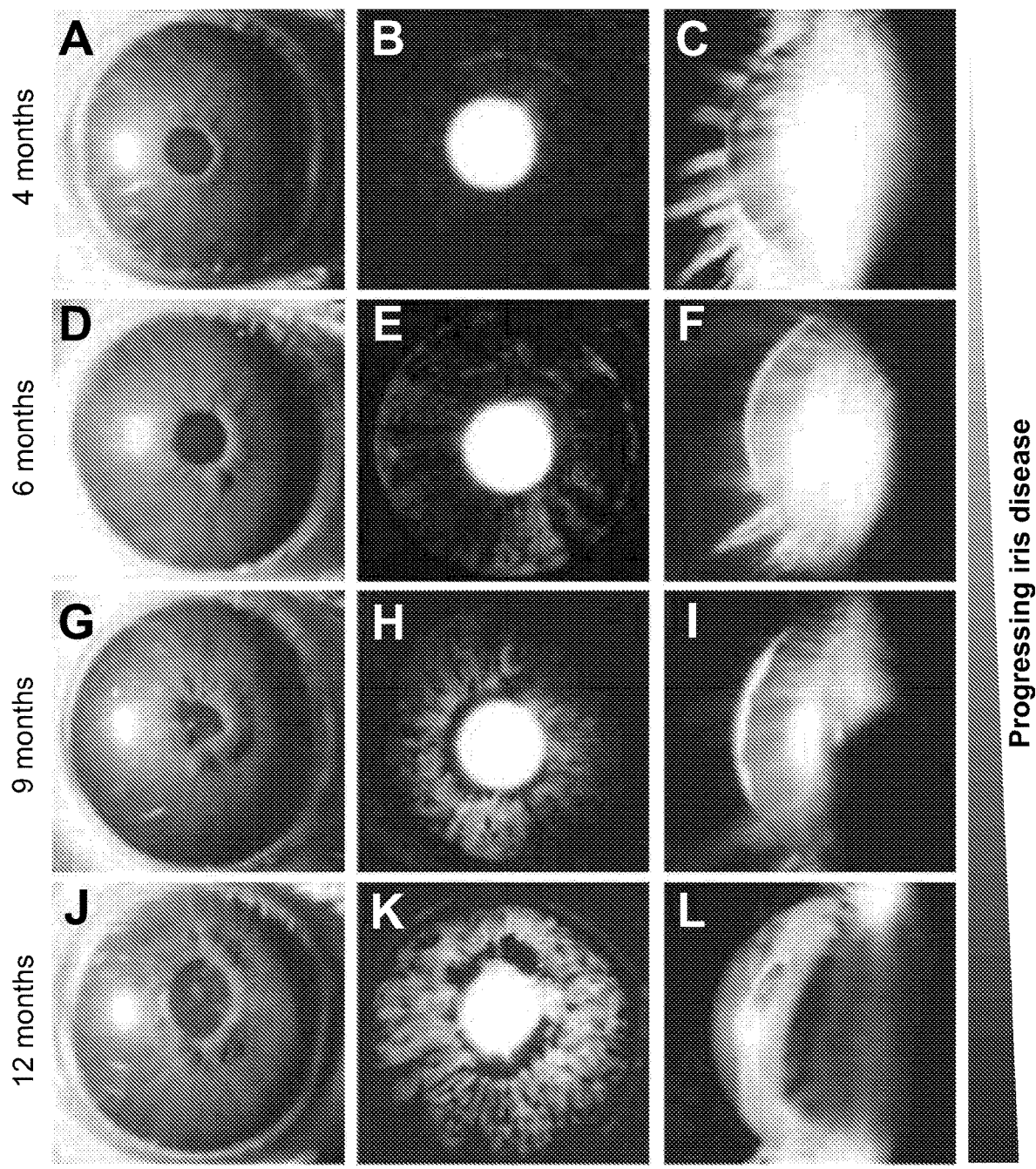
FIGS. 1A-1L show progression of iris disease in DBA/2J mouse eyes. Each row contains three images of the same eye, showing on the left broad beam illumination images, in the center trans-illumination images (which represent reflected light passing through depigmented areas of the iris), and on the right anterior chamber images. At 4 months, iris disease was not evident (FIGS. 1A-1C). From 6 months of age, DBA/2J eyes developed a progressing iris disease characterized by iris atrophy and pigment dispersion (FIGS. 1D-1F). Trans-illumination (FIG. 1E) was detectable and there was slight enlargement of the anterior chamber (FIG. 1F). By 9 months, iris disease had progressed, there was evident swelling of the peripupillary tissue (surrounding the pupil, FIG. 1G), significant trans-illumination (FIG. 1H), and enlargement of the anterior chamber (FIG. 1I). By 12 months, this had progressed further (FIGS. 1J-1L) and dispersed iris pigment was evident on the cornea and lens (FIG. 1J).

By 6 months of age, mild iris disease had started to occur, and was evident through mild swelling in peripupillary, the inside of the iris that forms the pupil (FIG. 1D), and mild trans-illumination defects (FIG. 1E). Trans-illumination measures reflected light passing through depigmented areas of the iris. The more reflected light, the greater the severity of the iris disease.

By 9 months of age, peripupillary swelling was pronounced, clumps of pigment were present in the anterior chamber (FIG. 1G), and there were more moderate trans-illumination defects (FIG. 1H) and enlargement of the anterior chamber (FIG. 1I).

Iris disease was severe by 12 months of age (FIGS. 1J-1L), with substantial pigment dispersion, profound trans-illumination defects, and enlarged anterior chambers.

Figure 2:
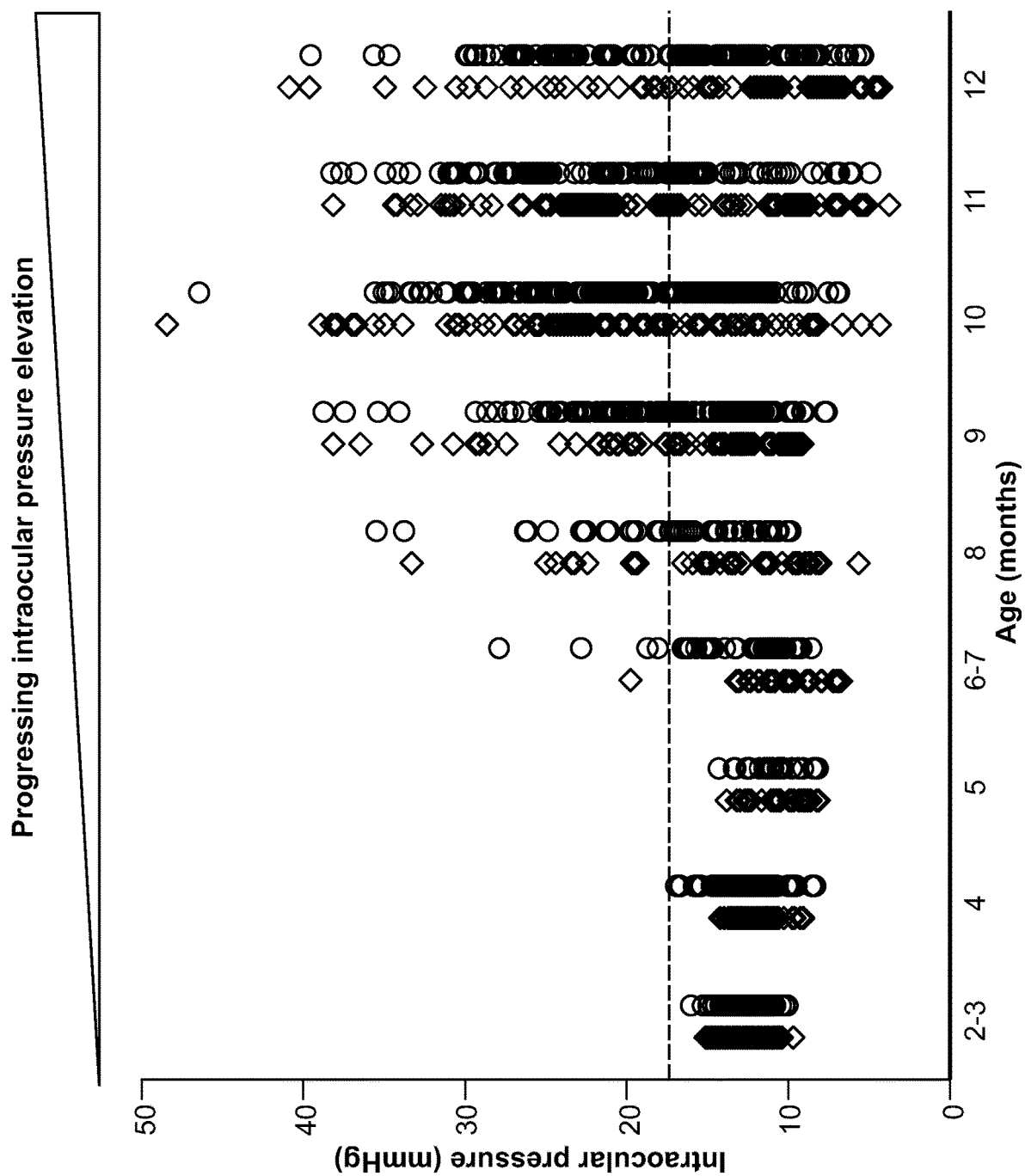
FIG. 2 shows intraocular pressure (IOP) profile in DBA/2J mouse eyes. High intraocular pressure was first detected around 6-7 months of age. The majority of eyes had high intraocular pressure by 9 months of age, which persisted until 12 months of age. By 12 months of age, the majority of mice had developed severe glaucoma/glaucomatous neurodegeneration. Diamonds show female values, Circles show male values. Female mice tend to develop high intraocular pressure earlier than males. Dotted line represents 3 standard deviations from the mean of the 2-3 month group.

Example 2 Progressive Iris Disease Leads to Increased Intraocular Pressure in DBA/2J Eyes Following the onset of iris disease around 6 months of age, intraocular pressure began to increase (FIG. 2). A typical "normal" IOP in a D2 mouse eye is ~13 mmHg, which increases progressively from 6 to 12 months, to values that can typically exceed 20 mmHg. By 9 months of age, IOP was/had been elevated in the majority of the eyes of the D2 mice. IOP increases in D2 eyes were age-related and asynchronous, as well as being highly variable. In our colony, females tend to have higher/early onsets of elevated IOP (FIG. 2).

Example 3 Eyes of DBA/2J Mice Have Progressive Visual Dysfunction as Assessed by Pattern Electroretinography (PERG)

The retinal ganglion cells (RGCs) are the output neuron of the retina, and their axons make up the optic nerve. Retinal ganglion cells are specifically affected during periods of intraocular pressure that manifests as visual dysfunction prior to gross histological defects, including retinal ganglion cell loss and degeneration of the optic nerve).

Figure 3:
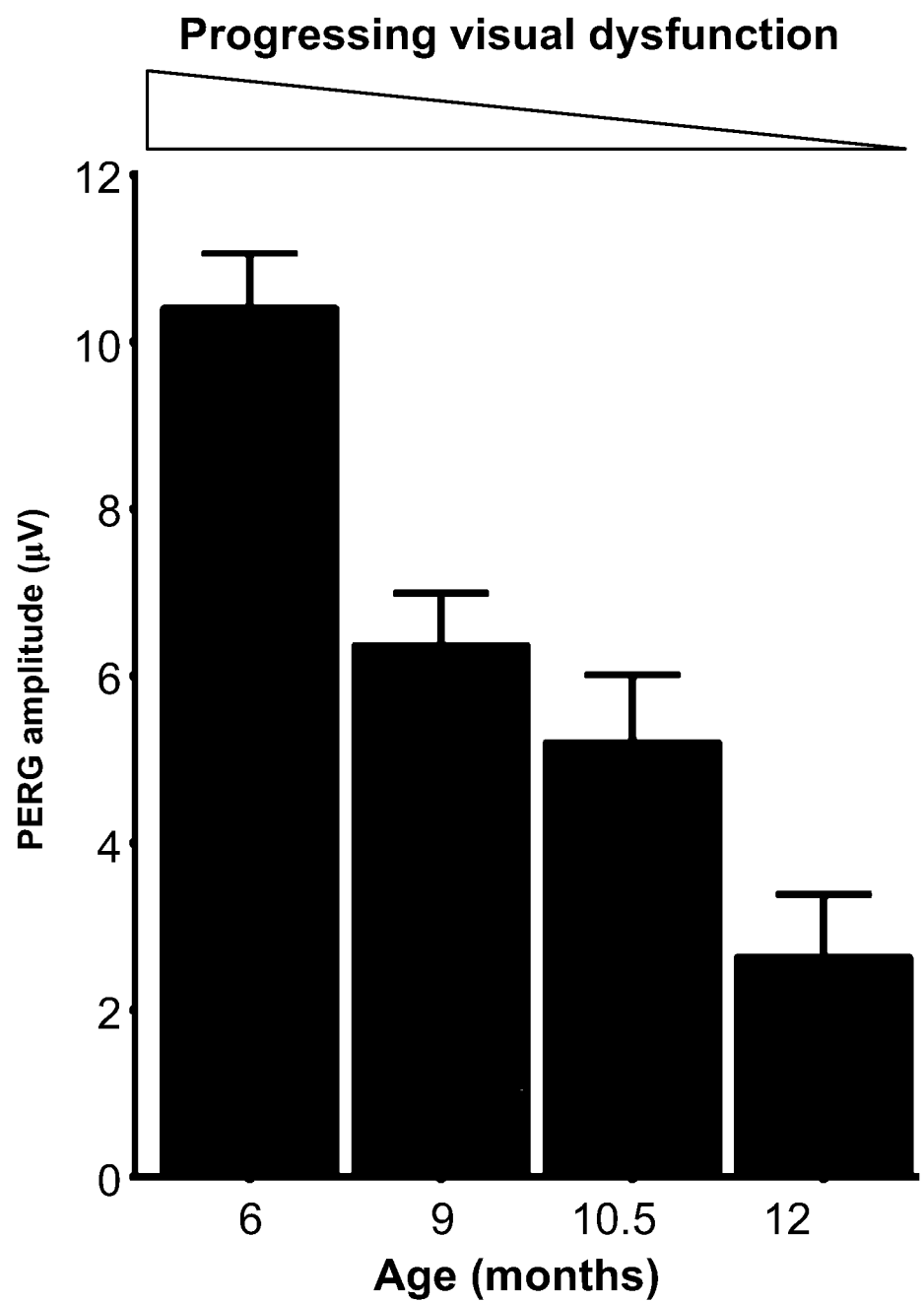
FIG. 3 shows loss of visual sensitivity in DBA/2J mouse eyes. Following an increase in intraocular pressure, there was a significant decrease in visual sensitivity in DBA/2J eyes as assessed by pattern electroretinography (PERG). This loss of function was closely associated with the progressive increase in intraocular pressure. By 12 months of age, PERG amplitude had decreased into the noise range (i.e., little-to-no detectable physiological function). PERG is a sensitive measure of visual function, and this visual dysfunction likely occurred prior to gross histological changes (cell loss, axon degeneration, etc). In human glaucoma, PERG amplitude losses are larger than retina nerve fiber layer loss as typically assessed by OCT.

In this example, we used pattern electroretinography (PERG) to measure retinal ganglion cell health in order to detect decreases in visual function prior to degeneration of the optic nerve. PERG assessment of D2 eyes (FIG. 3) demonstrated a progressive loss of visual function that is significant from 9 months of age, which is the time when the majority of the D2 mice eyes had/have had elevated IOP, but is prior to any retinal ganglion cell loss or axon degeneration in the optic nerve. As is shown in FIG. 3, by 12 months of age, PERG amplitude was indistinguishable from noise, signifying no detectable visual function.

Example 4 Retinal Ganglion Cells Degenerate Following Prolonged Periods of Elevated Intraocular Pressure To determine the fate of the retinal ganglion cells following prolonged period of elevated IOP in the D2 mice, we used PPD staining of the optic nerve to reveal the extent of retinal and/or optic nerve neurodegeneration, as PPD darkly stains the axoplasm of dead/dying axons.

Figure 4:
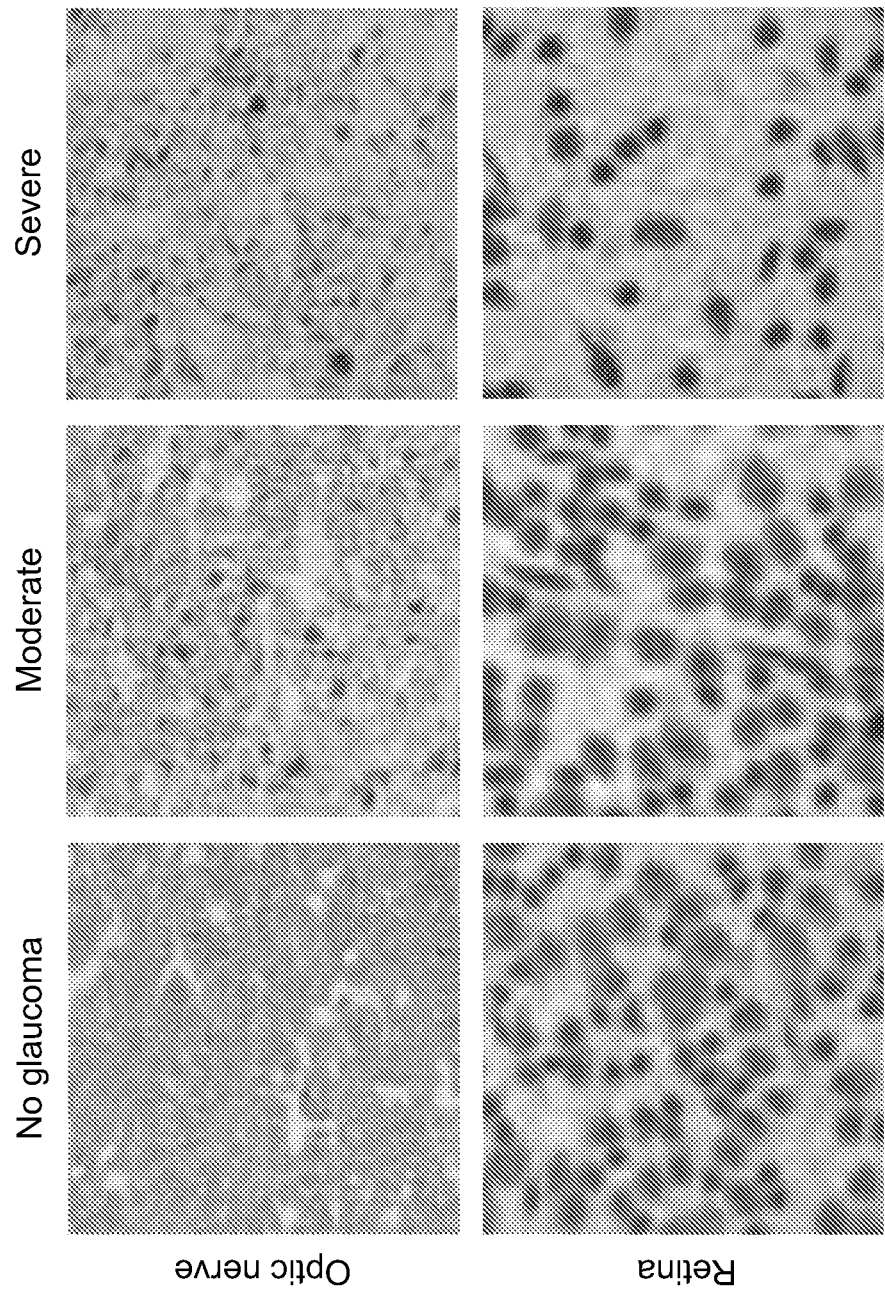
FIG. 4 shows results of histological examination of DBA/2J optic nerve and retina. A typical DBA/2J study was terminated at 12 months of age where the majority of eyes (>70%) had severe glaucoma as assessed by PPD staining of the optic nerve. PPD darkly stains the axoplasm of dying/ dead axons. Top row, PPD staining of optic nerves from 12 month old DBA/2J eyes. In the minority of DBA/2J eyes that had not developed glaucoma by 12 months of age there was no staining of axons in the optic nerve (left). Once glaucoma had progressed to moderate (>20% axon loss) and severe (>50% axon loss) glaucoma, there was evident staining of dying/dead axons in the optic nerve. These findings were correlated in the retina as assessed by Nissl staining (neuronal stain; bottom row). In eyes that had not yet developed glaucoma, there was no loss of retinal ganglion cells in the inner retina. Once glaucoma had progressed to moderate and severe disease, there was significant retinal ganglion cell loss within the inner retina.

As shown in FIG. 4, upper row, PPD staining of the optic nerve showed that the majority (~70%) of the D2 mice eyes had severe glaucoma at about 12 months of age, when an experiment using our colony of D2 mice typically ends. For this purpose, we distinguished optic nerves as having one of three levels of damage: no glaucoma, where there is <5% axon loss in the optic nerve, these nerves are indistinguishable from young controls; moderate glaucoma, with <20% axon loss, and evidence of darkly stained axons; or severe glaucoma, with >50% axon loss, and typically accompanied by gliosis/gliotic scarring.

The findings in the optic nerve were paralleled in the retina. As shown in FIG. 4, lower row, retinal ganglion cell soma loss was undetectable in "no glaucoma" D2 mice eyes, but significant in D2 mice eyes having been assessed as having "severe glaucoma."

At 9 months of age, all eyes in our colony have "no glaucoma," as assessed by optic nerve grading and retinal ganglion cell counts (data not shown), yet there are early molecular changes and defects in visual function as assessed by PERG. See Example 3.

Example 5 Genes/Pathways Analysis Reveals Mitochondria Defect in Early Glaucoma and Shift to Fatty Acid Metabolism with Fat Droplet Deposit in Retina To identify susceptible genes/pathways leading to glaucoma, we performed RNA-sequencing (RNA-seq) from RNA of RGCs obtained from isolated retina of: (i) 4-month old DBA/2J D2 mice, (ii) 9-month old DBA/2J D2 mice, and (iii) age-, sex-, and strain-matched D2-Gpnmb+ wild-type controls, in order to elucidate very early molecular changes within the RGCs that precede neurodegeneration.

The 4-month old D2 mice were verified to exhibit normal intraocular pressure (IOP) (i.e., 10-13 mmHg) and no glaucoma (i.e., these mice were at an age preceding the development of IOP and pre-glaucoma; no detectable neurodegeneration). At this age, D2 mice are indistinguishable from control mice.

The 9-month old D2 mice were verified to exhibit high IOP (i.e., >21 mmHg) but no neurodegeneration (see Examples 3 and 4). Although conventional glaucoma is absent at this developmental stage (i.e., pre-neurodegeneration), eyes in the 9-month old D2 mice undergo molecular changes defined as having "early glaucoma" herein.

The control D2-Gpnmb+ mice were used in this study, because these mice exhibit neither high IOP nor neurodegeneration with aging. These mice are identical to D2 mice except for a correction of the iris disease causing $Gpnmb^{R150X}$ mutation.

Amplified dscDNA libraries (double-stranded copy DNA) generated from RNA and read at a depth of 35 million reads per sample. Data analysis was performed at a false discovery rate (FDR, q) of q<0.05. All samples were successfully amplified and sequenced.

Unsupervised hierarchical clustering (HC) was then used to define molecularly determined stages of glaucoma among samples that are at initial stages of disease and morphologically indistinguishable from age-matched D2-Gpnmb+ or young controls.

This analysis revealed that, as disease progressed, there was an increase in transcript abundance that was most pronounced for mitochondrial reads, with significant enrichment of differentially expressed genes in the mitochondrial dysfunction and oxidative phosphorylation pathways, suggesting mitochondrial abnormalities within RGCs (data not shown). Mitochondrial dysfunction was confirmed through targeted metabolic assays and electron microscopy (EM), showing abnormal mitochondria early in glaucoma along with an early energy crisis.

These data suggest that RGCs go through a period of mitochondrial stress and metabolite depletion, potentially moving towards fatty acid metabolism, corresponding with an increase in lipid deposits in the retina during early glaucoma.

As shown in FIG. 5A, extracellular lipid/fat droplet formation was apparent in the inner-retina of IOP-insulted, aged (about 12 months old) D2 mice eyes, as revealed by staining with Oil Red O (which brightly stains neutral triglycerides and lipids). Staining was present in D2 mice eyes that had no optic nerve degeneration (NOE) or had severe (SEV) optic nerve degeneration. Extra-ocular fat was used as a positive control.

FIG. 5B shows progression of lipid droplet formation in D2 mice retinas. Again, lipid/fat droplet formation in the inner retina was assessed by Oil Red O staining. Following intraocular pressure elevation, lipid droplets were present within the inner retina of D2 mice. At 6 months of age, the majority of retinas were negative for lipid droplets. By 9 months of age, small and dispersed lipid droplets were present in some eyes. By 12 months of age, lipid accumulation was present in the majority of eyes in retinas that had not yet developed glaucoma (no glaucoma). In eyes that had developed severe glaucoma, lipid droplets were present across the retina in the majority of the D2 mice eyes.

Intraocular pressure had been present in "no glaucoma" eyes, yet typical measures of glaucomatous damage, e.g., axon loss, retinal ganglion cell loss, decreases in PERG amplitude, were not yet present. However, these "no glaucoma" eyes had significant lipid droplet deposits, suggesting that lipid accumulation could be an early stage biomarker useful for diagnosing early glaucomatous pathogenesis.

Example 6 NAM Alleviates Glaucoma in D2 Mice and Prevents Fat Droplet Formation We have separately discovered that nicotinamide (NAM), a precursor of NAD, can be administered to D2 mice in drinking water (550 mg/kg/d, NAM or $NAM^{Lo}$), in order to prevent the decline of NAD levels and to protect the D2 mice from all detectable signs of glaucoma through 12 months, a standard end stage for assessing neurodegeneration in this glaucoma mouse model. Other neuroprotective agents, such as pyruvate, were found to have similar neuroprotective functions as NAM (See FIG. 6).

To further demonstrate the usefulness of the lipid/fat droplet deposit in inner retina as a biomarker for glaucomatous pathogenesis, we designed this experiment to show that therapeutic intervention using nicotinamide (NAM) simultaneously prevented/alleviated glaucoma progression as well as fat droplet formation.

We conducted this in vivo experiment using a large cohort of D2 mice. In this experiment, optic nerves were classified into three damage levels: NO (no glaucoma), MOD (moderate damage), and SEV (severe damage).

Experimental D2 mice were divided into the following groups and were given:

W=water (standard mouse water)
NAM or $NAM^{Lo}$=550 mg/kg/d NAM in drinking water
Early=early start=pre-glaucoma=6-month of age (i.e. prophylactic)
Late=late start=during glaucoma=9-month of age (when mice already have high IOP, i.e. interventional, and more relative to human glaucoma)

Mice were then assessed at 12-month for optic nerve damage, soma loss, visual function, and axonal transport (data not shown).

Supporting the neuronal vulnerability hypothesis, NAM did not alter IOP (data not shown), but it robustly protected D2 mice from developing glaucoma, i.e. NAM is a neuroprotective agent. Importantly, NAM was protective both prophylactically (starting at 6-month, early start; prior to IOP elevation in the vast majority of eyes in the colony), and as an intervention (starting at 9-month, late start; when the majority of eyes have had continuing IOP elevation). This signifies that NAM is able to both prevent neuronal injury from occurring as well as limiting neuronal injury to already insulted neurons (FIG. 6). This is important for human disease where treatment would only start once a disease has become symptomatic and thus detectable.

These data support that NAM can be used prophylactically to treat human glaucoma, either in subjects at risk of glaucoma, for example, due to family history, ocular trauma, known gene mutation, or when IOP is seen to be higher but no glaucomatous damage is present.

In addition, NAM may also be used prophylactically to treat human glaucoma, when damage is already present or beginning to manifest, as different cells succumb at different times.

NAM was also shown to robustly prevent retinal ganglion cell dysfunction and degeneration (data not shown), protects early synapse loss (data not shown), inhibits the formation of dysfunctional mitochondria with abnormal cristae (data not shown); prevents age-related gene expression In RGCs (data not shown), as well as decreases PARP activation and prevents molecular signs of glaucoma based on immunostaining (data not shown).

In the majority of the treated eyes, NAM administration completely prevents glaucoma, including results based on very sensitive measures of early disease such as PERG. In addition, many ocular and neurodegenerative diseases occur in the elderly due to age-dependent molecular chances that increase susceptibility to damage. NAM treatment prevents age-related molecular changes assessed by gene expression (a very sensitive measure of these changes). Furthermore, axonal degeneration and somal shrinkage may represent common components in some neurodegenerative diseases. NAM prevents these changes based on the data above at least in glaucoma treatment. Furthermore, the data above shows that NAM prevents axonal degeneration and somal shrinkage in glaucoma.

Meanwhile, FIG. 7 shows that nicotinamide (NAM) prevents lipid deposit accumulation in DBA/2J retinas. Lipid droplet formation was assessed in retinas from nicotinamide-treated DBA/2J mice. Lipid droplet accumulation (red) was present in retinas from untreated 12 month of age DBA/2J mice, and was completely prevented in all retinas from nicotinamide-treated DBA/2J mice.

This data establishes a strong correlation between the presence and amount/extent of fat droplets and early glaucomatous pathogenesis, making fat droplets a useful biomarker that can be used for diagnosing, prognosing, and monitoring glaucoma, especially retinal and/or optic nerve neurodegeneration in glaucoma.

Example 7 In Vivo Detection of Oil Droplet in Glaucomatous Mice

In this example, we provide proof of principle of the ability to label and detect lipid droplets in the retina and optic nerve in glaucoma in vivo. In this study, we administered a fluorescent lipophilic stain (Nile Red; also known as Nile Blue oxazone) to glaucomatous mice in vivo, allowing lipophilic staining for the in vivo detection of lipid droplets using standard ophthalmic procedures of dye injection followed by fluorescent ocular imaging using scanning laser ophthalmoscopes. Nile Red is used to label lipids, lipoproteins, phospholipids, and sphingolipids in histological samples. Nile Red is solvatochromic (changes wavelength based on solvent polarity) and fluoresces deep red when bound to polar lipids and yellow/orange when bound to neutral lipids. In other words, Nile Red will not fluoresce in most polar solvents; however, when in a lipid-rich environment can be intensely fluorescent with varying colors from deep red (for polar lipids) to strong yellow-gold emission (for neutral lipid e.g. in intracellular storage). It should be noted that other fundal imaging modalities may be used.

Here, instead of using a scanning laser ophthalmoscope or fundus camera with the requisite excitation and emission filters for detecting the lipophilic fluorescent dye (e.g., Nile Red), we used a confocal microscope to detect in vivo Nile Red stained lipid droplets in the retina and optic nerve of glaucomatous mice. To label lipid droplets in vivo in glaucoma, anaesthetized DBA/2J (D2) mice were administered 1.5 μl Nile Red (10 mM) in sterile saline by intravitreal injection. Twenty minutes after injection, mice were euthanized, retinas dissected, and counterstained with DAPI (nuclear counterstain). Retinas of mice were examined by confocal microscopy with the appropriate emission and excitation filters for detecting Nile Red fluorescence.

As shown in FIG. 8, Nile Red strongly labeled and detected lipid droplets in DBA/2J mice that are developing glaucoma (10.5 months of age when most eyes have high IOP and are at early stages of glaucoma). The eye with early glaucoma was readily distinguishable from no-glaucoma control eyes, which essentially lacked the lipid droplets. Using fluorescent confocal microscope, the present study points to an important and significant diagnostic application for lipid droplets as eyes at early stages of glaucoma are not otherwise distinguishable from controls (no-glaucoma) using state-of-the-art conventional measures.

Example 8 In Vivo Detection of Oil Droplet in Glaucomatous Human

In humans, the retina and optic nerve and their vasculature are regularly monitored using fluorescent stains that can be applied by various means including intravitreal injection, intravenous injection, or iontophoresis. Intravitreal injections are safe and are commonly used in ophthalmic practice with a recent surge in treatments administered by this route and individual eyes being treated by such injection every 4 to 8 weeks. Topical application to the eye or other modes of delivery may also be used.

The lipophilic stains Nile Red or Indocyanine green (ICG) have been to used to label lipids in vivo in mice and other species, for example in atherosclerotic plaques. ICG is already approved for human use and is commonly used in standard practice for in vivo fluorescent monitoring of the human retina and its vessels. Other suitable lipophilic stains may be used to detect lipid droplets in humans. Optimal time for application of lipophilic stain can be conveniently determined by a skilled physician. For example, 20-60 minutes or days may be used. Repeated stain administration may also be performed to allow maximal build-up of stain in oil droplets for ease in clinical imaging. By using the appropriate near infrared excitation and emission filters, it is believed that ICG can be used as a new modality for detecting lipid droplets in the eye. In the human clinic, other suitable lipophilic dyes can be administered by a standard route and the lipid droplets monitored in vivo using a scanning laser ophthalmoscope or the other fluorescent fundal imaging modalities and the appropriate filters.

Our mouse study demonstrates the ability to label and observe lipid droplets in vivo. The mouse study directly translates feasibility of detecting and monitoring lipid droplets in humans. This has significant clinical application in detecting and monitoring glaucoma progression and effects of treatments in millions of glaucomatous subjects. Clinical biomicroscopes (including ophthalmoscopes) and filters for in vivo imaging can provide a useful diagnostic tool to detect lipid droplets in retina and optic nerve in humans. Fluorescent clinical imaging also provides a standard practice in combination with lipophilic stains. This provides widespread use in human clinical ophthalmology. Our glaucomatous mouse study using lipophilic stain to label lipid droplets in vivo demonstrates the feasibility of clinical application in humans.

Our study illustrates, for the first time, that lipid droplet detection may inform treatment decisions by allowing stratification of individuals with high IOP or other glaucoma risk factors, but who have not yet developed any neural damage (e.g., the retina especially retinal ganglion cells). Currently, many of such people are treated unnecessarily as they never progress to glaucoma (subjecting them to unnecessary medication-based risks and expense). Clinicians are becoming more cautious but waiting to detect damage before treating adds the risk of not treating people until too late (early treatment is most effective). Lipid droplet screening in the eye is therefore useful in the general population to identify individuals who should be assessed more fully for glaucoma, and other ocular conditions, even if only in at-risk families.

All cited references are incorporated by reference. While specific embodiments of the present invention have been described in the foregoing, it will be appreciated by those skilled in the art that many equivalents, modifications, substitutions, and variations may be made thereto without departing from the spirit and scope of the invention as defined in the appended claims.

What is claimed is:

1. A method for diagnosing optic nerve neurodegeneration in a subject, the method comprising the steps of:
   a) providing a subject suspected of having optic nerve neurodegeneration; and,
   b) detecting the presence of fat droplets in a retinal region and/or optic nerve region of the subject, wherein the detecting comprises
      i) administering a fluorescent dye to the subject; and,
      ii) detecting fluorescence of the administered fluorescent dye in the retinal region and/or optic nerve region of the subject wherein the detected fluorescence indicates the presence of fat droplets in the retinal region and/or optic nerve region of the subject,
   wherein the presence of fat droplets in the retinal region and/or optic nerve region of the subject is indicative of and diagnostic for optic nerve neurodegeneration in the subject.

2. The method of claim 1, wherein the fluorescent dye is a lipophilic dye, such as Oil Red O, Nile Blue, Nile Red, SRFluor680, LD540, LipidGreen, ICG/indocyanine green, or fluorescent nanoprobe.

3. The method of claim 1, wherein the subject is having glaucoma, high IOP, or at risk of having glaucoma.

4. The method of claim 1, wherein the fluorescent dye is administered to the eye of the subject by intravitreal injection, intravenous injection, topical application, or iontophoresis.

5. The method of claim 1, wherein the fluorescent dye is administered into the eye two or more times.

6. The method of claim 1, wherein the fluorescent dye is detected after a set period time post administration of the fluorescent dye, wherein the set period of time is 3-5 minutes, about 10 minutes, 20-60 minutes, 1-3 hrs, 5-10 hrs, 12-24 hrs, 1 day, 2 days, 3 days, 4 days, 5 days or more.

7. The method of claim 1, wherein the fluorescent dye is detected in vivo using a non-invasive detection method selected from the group consisting of: Scanning Laser Ophthalmoscopy (SLO), fundoscopy (such as a fluorescent fundal imaging modality), and biomicroscope.

8. The method of claim 1, wherein the subject has a normal IOP value of <21 mmHg.

9. The method of claim 1, wherein the subject is an adult human, and optionally the adult human is over 40.

10. The method of claim 1, wherein the subject has no signs or symptoms of glaucoma, but is associated with a risk factor for developing glaucoma selected from the group consisting of: intraocular pressure (IOP), age, race or ethnic background, family history, gender, medical condition, eye condition, eye injury or surgery, early estrogen deficiency, corneal thickness, and corticosteroid medication.

11. The method of claim 1, wherein the subject is a patient seeking routine annual eye examination.

12. The method of claim 1, wherein step b) is carried out using fundoscopy, OCT (Optical coherence tomography), Scanning Laser Ophthalmoscopy (SLO), Adaptive Optics SLO (AOSLO), or Raman spectroscopy, optionally in combination with using one or more fluorescent marker dyes or other agents that highlight the lipid droplets.

13. The method of claim 1, further comprising selecting the subject for receiving treatment for glaucoma when the retinal region is found to have fat droplets.

14. A method for prognosing ocular neurodegeneration in glaucoma, the method comprising the steps of:
   a) providing a subject having glaucoma and/or having a high intraocular pressure (IOP); and,
   b) detecting the presence and optionally the amount of fat droplets in a retinal region and/or optic nerve region of the subject, wherein the detecting comprises
      i) administering a fluorescent dye to the subject and
      ii) detecting fluorescence of the administered fluorescent dye in the retinal region and/or optic nerve region of the subject wherein the detected fluorescence indicates presence of and optionally an amount of fat droplets in the retinal region and/or optic nerve region of the subject,
   wherein the presence and optionally the amount of fat droplets in the retinal region and/or optic nerve region of the subject is prognostic of ocular neurodegeneration in glaucoma in the subject.

15. A method for monitoring ocular neurodegeneration in glaucoma, the method comprising the steps of:
   a) providing a subject having neurodegeneration in glaucoma;
   b) detecting the presence and optionally the amount of fat droplets in a retinal region and/or optic nerve region of the subject, before and after a treatment or therapeutic intervention for ocular neurodegeneration is administered to the subject, wherein the detecting comprises
      i) administering a fluorescent dye to the subject; and,
      ii) detecting fluorescence of the administered fluorescent dye in the retinal region and/or optic nerve region of the subject wherein the detected fluorescence indicates the presence and optionally the amount of fat droplets in the retinal region and/or optic nerve region of the subject, c) comparing the presence and optionally the amount of fat droplets in the retinal region and/or optic nerve region of the subject before and after the treatment or therapeutic intervention is administered, and/or comparing the presence and optionally the amount of fat droplets in the retinal region and/or optic nerve region of the subject before and/or after the treatment or therapeutic intervention is administered to a control amount of fat droplets in the retinal region and/or optic nerve region, thereby monitoring the ocular neurodegeneration in glaucoma in the subject.

16. The method of claim 1, further comprising:

comparing the presence of fat droplets detected in the retinal region and/or optic nerve region of the subject administered the fluorescent dye to a control presence fat droplets and selecting, continuing, or tailoring one or more ocular degeneration treatments for administration to the subject based on the comparing, optionally wherein the control presence is a presence of fat droplets detected in the retinal region and/or optic nerve region of the subject before a treatment or therapeutic intervention for ocular neurodegeneration in the subject.

17. The method of claim 14, further comprising:

comparing the presence and optionally the amount of fat droplets detected in the retinal region and/or optic nerve region of the subject to a control presence and optionally a control amount of fat droplets detected, respectively and selecting, continuing, or tailoring one or more glaucoma treatments for administration to the subject based on the comparing, optionally wherein the control presence and the amount are a presence and amount of fat droplets detected in the retinal region and/or optic nerve region of the subject before a treatment or therapeutic intervention for ocular neurodegeneration in glaucoma is administered to the subject.

18. The method of claim 15, further comprising:

selecting, continuing, or tailoring one or more glaucoma treatments for administration to the subject based on the comparing.

19. The method of claim 10, wherein the medical condition is diabetes, heart disease, high blood pressure or sickle cell anemia; the eye condition is myopia or hyperopia; and the corticosteroid medication comprises eye drops comprising corticosteroid medication.

* * * * *